(12) United States Patent
Liu et al.

(10) Patent No.: US 8,961,964 B2
(45) Date of Patent: Feb. 24, 2015

(54) HIGH CONCENTRATION ANTIBODY AND PROTEIN FORMULATIONS

(75) Inventors: Jun Liu, Pacifica, CA (US); Steven J. Shire, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/165,643

(22) Filed: Jun. 21, 2011

(65) Prior Publication Data

US 2012/0064086 A1     Mar. 15, 2012

Related U.S. Application Data

(63) Continuation of application No. 12/197,005, filed on Aug. 22, 2008, now abandoned, which is a continuation of application No. 10/813,483, filed on Mar. 29, 2004, now abandoned.

(60) Provisional application No. 60/460,659, filed on Apr. 4, 2003.

(51) Int. Cl.
*A61K 39/395* (2006.01)
*C07K 16/42* (2006.01)
*A61K 9/00* (2006.01)
*A61K 47/18* (2006.01)
*A61K 47/26* (2006.01)

(52) U.S. Cl.
CPC .......... *C07K 16/4291* (2013.01); *A61K 9/0019* (2013.01); *A61K 39/39591* (2013.01); *A61K 47/183* (2013.01); *A61K 47/26* (2013.01); *Y10S 435/80* (2013.01)
USPC ...................... 424/130.1; 424/133.1; 435/800

(58) Field of Classification Search
None
See application file for complete search history.

(56) References Cited

U.S. PATENT DOCUMENTS

| | | | |
|---|---|---|---|
| 4,093,606 A | 6/1978 | Coval | |
| 4,374,763 A | 2/1983 | Takagi | |
| 4,499,073 A | 2/1985 | Tenold | |
| 4,877,608 A | 10/1989 | Lee et al. | |
| 4,940,782 A | 7/1990 | Rup et al. | |
| 5,096,885 A | 3/1992 | Pearlman et al. | |
| 5,215,743 A | 6/1993 | Singh et al. | |
| 5,252,480 A | 10/1993 | Yokota et al. | |
| 5,262,296 A | 11/1993 | Ogawa et al. | |
| 5,328,694 A | 7/1994 | Schwinn | |
| 5,399,670 A | 3/1995 | Bhattacharya et al. | |
| 5,580,856 A | 12/1996 | Prestrelski et al. | |
| 5,608,038 A | 3/1997 | Eibl et al. | |
| 5,612,315 A | 3/1997 | Pikal et al. | |
| 5,849,700 A | 12/1998 | Sorenson et al. | |
| 5,871,736 A | 2/1999 | Bruegger et al. | |
| 5,994,511 A | 11/1999 | Lowman et al. | |
| 6,013,773 A | 1/2000 | Kobayashi et al. | |
| 6,037,453 A | 3/2000 | Jardieu et al. | |
| 6,096,872 A | 8/2000 | Van Holten et al. | |
| 6,172,213 B1 | 1/2001 | Lowman et al. | |
| 6,252,055 B1 | 6/2001 | Relton | |
| 6,267,958 B1 | 7/2001 | Andya et al. | |
| 6,290,957 B1 | 9/2001 | Lowman et al. | |
| 6,329,509 B1 | 12/2001 | Jardieu et al. | |
| 6,440,426 B1 | 8/2002 | Wheeler et al. | |
| 6,541,606 B2 | 4/2003 | Margolin et al. | |
| 6,682,735 B2 | 1/2004 | Lowman et al. | |
| 6,685,939 B2 | 2/2004 | Jardieu et al. | |
| 6,685,940 B2 | 2/2004 | Andya et al. | |
| 6,699,472 B2 | 3/2004 | Jardieu et al. | |
| 6,723,833 B1 | 4/2004 | Lowman et al. | |
| 6,875,432 B2 | 4/2005 | Liu et al. | |
| 7,157,085 B2 | 1/2007 | Lowman et al. | |
| 8,142,776 B2 * | 3/2012 | Liu et al. ................... | 424/130.1 |
| 2002/0045571 A1 | 4/2002 | Liu et al. | |
| 2003/0092607 A1 | 5/2003 | Carpenter et al. | |
| 2003/0113316 A1 | 6/2003 | Kaisheva et al. | |
| 2003/0138417 A1 | 7/2003 | Kaisheva et al. | |
| 2004/0019243 A1 | 1/2004 | Nightingale et al. | |
| 2004/0191243 A1 | 9/2004 | Chen et al. | |
| 2004/0197324 A1 | 10/2004 | Liu et al. | |
| 2005/0158303 A1 | 7/2005 | Liu et al. | |
| 2005/0175603 A1 | 8/2005 | Liu et al. | |
| 2006/0051347 A1 | 3/2006 | Winter | |
| 2006/0127395 A1 | 6/2006 | Arvinte et al. | |
| 2007/0053900 A1 | 3/2007 | Liu et al. | |
| 2007/0086995 A1 | 4/2007 | Liu et al. | |
| 2007/0116700 A1 | 5/2007 | Liu et al. | |
| 2008/0071063 A1 | 3/2008 | Allan et al. | |

(Continued)

FOREIGN PATENT DOCUMENTS

CA       2138853 A1    6/1995
EP       0 117 060 A2    8/1984

(Continued)

OTHER PUBLICATIONS

US 5,036,049, 7/1991, Audhya et al. (withdrawn).
Arakawa et al. (1991). "Protein-Solvent Interactions in Pharmaceutical Formulations" *Pharmaceutical Research* 8(3):285-291.
Bam et al. (1995). "Stability of Protein Formulations: Investigation of Surfactant Effects by a Novel EPR Spectroscopic Technique," *Pharmaceutical Research* 12:2-11.
Breen, E.D. et al. (Sep. 2001). "Effect of Moisture on the Stability of a Lyophilized Humanized Monoclonal Antibody Formulation," *Pharmaceutical Research* 18(9):1345-1353.

(Continued)

*Primary Examiner* — Yunsoo Kim
(74) *Attorney, Agent, or Firm* — Morrison & Foerster LLP

(57) ABSTRACT

The present application relates to highly concentrated antibody and protein formulations with reduced viscosity that are stable, relatively isotonic and are of low turbidity. The formulations are particularly suitable for subcutaneous administration. The application further describes articles of manufacture containing such formulations and method for using them to treat disorders treatable by the formulated antibody or protein.

14 Claims, 7 Drawing Sheets

(56) References Cited

U.S. PATENT DOCUMENTS

| | | | |
|---|---|---|---|
| 2009/0060906 A1 | 3/2009 | Barry et al. | |
| 2009/0169544 A1 | 7/2009 | Nilsson et al. | |
| 2009/0280129 A1 | 11/2009 | Liu et al. | |
| 2010/0158898 A1 | 6/2010 | Liu et al. | |
| 2010/0239567 A1 | 9/2010 | Esue | |

FOREIGN PATENT DOCUMENTS

| | | | |
|---|---|---|---|
| EP | 0 117 060 A3 | 8/1984 | |
| EP | 0 303 746 A1 | 2/1989 | |
| EP | 0 303 746 B1 | 2/1989 | |
| EP | 0 303 746 B2 | 2/1989 | |
| EP | 0 391 444 A2 | 10/1990 | |
| EP | 0 391 444 A3 | 10/1990 | |
| EP | 0 531 539 A1 | 3/1993 | |
| EP | 0 631 539 B1 | 3/1993 | |
| EP | 0 597 101 A1 | 5/1994 | |
| EP | 0 597 101 B1 | 5/1994 | |
| EP | 0 661 060 A2 | 7/1995 | |
| EP | 0 661 060 A3 | 7/1995 | |
| EP | 0 661 060 B1 | 7/1995 | |
| EP | 0 787 497 A2 | 8/1997 | |
| EP | 0 787 497 A3 | 8/1997 | |
| EP | 0 841 067 A1 | 5/1998 | |
| EP | 0 841 067 B1 | 5/1998 | |
| EP | 0 909 564 A1 | 4/1999 | |
| EP | 0 909 564 B1 | 4/1999 | |
| EP | 1 197 221 A1 | 4/2002 | |
| EP | 1 197 221 B1 | 4/2002 | |
| EP | 1 325 751 A1 | 7/2003 | |
| EP | 2 335 725 A1 | 6/2011 | |
| JP | 7-206709 A | 8/1995 | |
| JP | 2001-503781 A | 3/2001 | |
| WO | WO-89/11297 A1 | 11/1989 | |
| WO | WO-90/11091 A1 | 10/1990 | |
| WO | WO-92/17207 A1 | 10/1992 | |
| WO | WO-93/04173 A1 | 3/1993 | |
| WO | WO-93/05799 A1 | 4/1993 | |
| WO | WO-96/20202 A1 | 4/1996 | |
| WO | WO-97/04801 A1 | 2/1997 | |
| WO | WO-97/45140 A1 | 4/1997 | |
| WO | WO-97/26909 A1 | 7/1997 | |
| WO | WO-98/22136 A2 | 5/1998 | |
| WO | WO-98/22136 A3 | 5/1998 | |
| WO | WO-99/01556 A2 | 1/1999 | |
| WO | WO-99/01556 A3 | 1/1999 | |
| WO | WO-00/15260 A1 | 3/2000 | |
| WO | WO-02/12501 A2 | 2/2002 | |
| WO | WO-02/30463 A2 | 4/2002 | |
| WO | WO-02/30463 A3 | 4/2002 | |
| WO | WO-02/30464 A1 | 4/2002 | |
| WO | WO-02/072636 A2 | 9/2002 | |
| WO | WO-02/072636 A3 | 9/2002 | |
| WO | WO-02/096457 A2 | 12/2002 | |
| WO | WO-02/096457 A3 | 12/2002 | |
| WO | WO-03/009817 A2 | 2/2003 | |
| WO | WO-03/039485 A2 | 5/2003 | |
| WO | WO-2004/091658 A1 | 10/2004 | |
| WO | WO-2006/065746 A2 | 6/2006 | |
| WO | WO-2006/065746 A3 | 6/2006 | |

OTHER PUBLICATIONS

Carpenter et al. (1997). "Rational Design of Stable Lyophilized Protein Formulations: Some Practical Advice," *Pharmaceutical Research* 14(8):969-975.

Casolaro, V. et al. (1993). "Release from Human Basopbils and Mast Cells" *J. of Pharmacology and. Experimental Therapeutics* 267(3):1375-1385.

Chang, L. et al. (Sep. 2009, e-pub. Jun. 30, 2009). "Mechanisms of Protein Stabilization in the Solid State," *Journal of Pharmaceutical Science* 98(9):2886-2908.

Chen, B. et al. (Dec. 2003). "Influence of Histidine on the Stability and Physical Properties of a Fully Human Antibody in Aqueous and Solid Forms" *Pharmaceutical Research* 20(12):1952-1960.

Cleland et al. (1993). "The Development of Stable Protein Formulations: A Close Look at Protein Aggregation, Deamidation, and Oxidation" *Critical Reviews in Therapeutic Drug Carrier Systems* 10(4):307-377.

Cleland et al. (1995). "Development of Stable Protein Formulations for Microencapsulation in Biodegradable Polymers," *Proceed. Intern. Symp. Control. Rel. Bioact. Mater.* 22:514-515.

Corne et al. (1997). "The Effect of Intravenous Administration of a Chimeric Anti-IgE Antibody on Serum IgE Levels in Atopic Subjects: Efficacy, Safety, and Pharmacokinetics," *J. Clin. Invest.* 99(5):879-887.

Daugherty, A.L. et al. (Jan. 1, 2010). "Formulation and Delivery Issues for Monoclonal Antibody Therapeutics," *Advanced Drug Delivery Reviews* 58:686-706.

Dráber et al. (1995). "Stability of Monoclonal IgM Antibodies Freeze-Dried in the Presence of Trehalose," *Journal of Immunological Methods* 181(1):37-43.

Garidel, P. et al. (2009, e-pub. Apr. 16, 2009). "A Thermodynamic Analysis of the Binding Interaction Between Polysorbate 20 and 80 With Human Serum Albumins and Immunoglobulins: A Contribution to Understand Colloidal Protein Stabilisation," *Biophysical Chemistry* 143:70-78.

Haecker, G. et al. (1994). "Proliferative and Cytolytic Responses of Human γδ T Cells Display a Distinct Specificity Pattern," *Immunology* 81:564-566.

He, F. et al. (Apr. 2010, e-pub. Sep. 24, 2009). "High Throughput Thermostability Screening of Monoclonal Antibody Formulations," *Journal of Phamaceutical Sciences* 99(4):1707-1720.

Holma, B. et al. (1989). "pH- and Protein-Dependent Buffer Capacity and Viscosity of Respiratory Mucus, Their Interrelationships and Influence on Health," *The Science of the Total Environment* 84:71-82.

Hudson, L. et al. (1980). *Practical Immunology*, Second Edition, Blackwell Scientific Publications, p. 336.

International Search Report mailed on Jun. 19, 2002, for PCT Application No. PCT/US01/42487, filed on Oct. 4, 2001, two pages.

Iwanaga, S. (1978). "1-2-1 Separation Method Making Use of Solubility," *New Lectures on Experimental Chemistry* 20(Biochemistry 1):14-26, Japanese language (English Translation, 16 pages).

Jones, A. (1993). "Analysis of Polypeptides and Proteins." *Adv. Drug Delivery Rev.* (10)29-90.

Kinekawa, Y-I. et al. (1998). "Effects of Salts on the Properties of Sols and Gels Prepared from Whey Protein Isolate and Process Whey Protein," *Journal of Dairy Science* 81(6):1532-1544.

Liu et al. (Sep. 2005). "Reversible Self-Association Increases the Viscosity of a Concentrated Monoclonal Antibody in Aqueous Solution" *Journal of Pharmaceutical Sciences* 94(9).

Loeb, J. (1921). "Donnan Equilibrium and the Physical Properties of Proteins," Chapter III, Viscosity, in *The Journal of General Physiology*, pp. 827-841. (55.00 series).

Loeb, J. (1921). "Donnan Equilibrium and the Physical Properties of Proteins," Chapter IV, Viscosity, in *The Journal of General Physiology*, pp. 73-95.

Mahler, H.R. et al. (1966). *Biological Chemistry*, Harper & Row Publishers, Inc.:New York, NY, Table 2.1, one page.

Manning et al. (1989). "Stability of Protein Pharmaceuticals" *Pharm. Res.* 6(11):903-918.

Mattern, M. et al. (1999). "Formulation of Proteins in Vacuum-Dried Glasses. II. Process and Storage Stability in Sugar-Free Amino Acid Systems," *Pharmaceutical Development and Technology* 4(2):199-208.

Merck Index (1983). 10th Ed., Merck & Co., Inc. pp. 797-798.

Milgrom, H. et al. (Dec. 23, 1999). "Treatment of Allergic Asthma with Monoclonal Anti-IgE Antibody. rhuMAb-E25 Study Group," *The New England Journal of Medicine* 341(26):1966-1973.

Nielsen, et al. (1995). "Stability of Freeze Dried Horseradish Peroxidase Conjugated Monoclonal Antibodies Used in Diagnostic Serology," *Journal of Immunoassay* 16(2):183-197.

Patapoff, T.W. et al. (2009). "Polysorbate 20 Prevents the Precipitation of a Monoclonal Antibody During Shear," *Pharmaceutical Development and Technology* 14(6):659-664.

Pearlman et al. (1991). "Analysis of Protein Drugs," Chapter 6 in *Peptide and Protein Drug Delivery*, Vincent H. L. Lee ed., Marcel Dekker, Inc., pp. 247-301.

(56) References Cited

OTHER PUBLICATIONS

Pikal et al. (1991) "The Effects of Formulation Variables on the Stability of Freeze-Dried Human Growth Hormone," *Pharmaceutical Research* 8:427-436.
Presented by The University of Colorado Center for Pharmaceutical Biotechnology, "2003 Colorado Protein Stability Conference," Breckenridge, Colorado (Jul. 17-19, 2003).
Presta et al. (Sep. 1, 1993). "Humanization of an Antibody Directed Against IgE" *J. Immunol.* 151(5):2623-2632.
Sampson, H.A. (2000). "Food Anaphylaxis," *British Medical Bulletin* 56(4):925-935.
Schneider, C. et al. (1990). "Some Viscosity Characteristics of Faba Bean Protein Isolats within a pH Range Relevant for Foods," *Die Nahrung* 34(8):735-745.
Simons, F.E.R. (2003). "What's in a Name? The Allergic Rhinitis—Asthma Connection," *Clinical and Experimental Alleergy Reviews* 3(1):9-17.
Tian, F. et al. (2007, e-pub. Jan. 19, 2006). "Calorimetric Investigation of Protein/Amino Acid Interactions in the Solid State," *International Journal of Pharmaceutics* 310:175-186.
Tian, F. et al. (2007, e-pub. Oct. 29, 2006). "Spectroscopic Evaluation of the Stabilization of Humanized Monoclonal Antibodies in Amino Acid Formulations," *International Journal of Phamaceutics* 335:20-31.
Tsumoto, K. et al. (Jul. 17-19, 2003). "Magic Agent for Protein Refolding and Solubilization: Arginine," *2003 Colorado Protein Stability Conference*, presented by the University of Colorado Center for the Pharmaceutical Biotechnology, Breckenridge, Colorado, Abstract Only, three pages.
U.S. Appl. No. 60/460,659, filed Apr. 4, 2003, by Liu et al.
U.S. Appl. No. 12/197,005, filed Aug. 22, 2008, by Liu et al.
U.S. Appl. No. 12/573,801, filed Oct. 5, 2009, by Liu et al.

Wagner, J.R. et al. (1992). "Effect of Physical and Chemical Factors on Rheological Behavior of Commercial Soy Protein Isolates: Protein Concentration, Water Imbibing Capacity, Salt Addition, and Thermal Treatment," *J. Agric. Food Chem.* 40:1930-1937.
Wang et al. (1988) "Parentera Formulations of Proteins and Peptides: Stability and Stabilizers," *J. Parenteral Sci. Tech.* (Technical Report No. 10)42(2S):S4-S26.
White et al. (1964). Principles of Biochemistry, 3rd edition, McGraw-Hill Company pp. 540.
Xu, X. et al. (1995). "Expression of Functional Insulin-Like Growth Factor-1 Receptor on Lymphoid Cell Subsets of Rats," *Immunology* 85:394-399. (Cited as Kuby in OA, p. 6).
Zietkiewicz et al. (1971). "In Vivo Studies on the Action on the Tissue of the Osmolality of Administered Drugs." *Grzyby Drozdzopodobne*. (English Translation Attached) 23:869-870.
Notice of Opposition and Brief, mailed on Jun. 10, 2011, for EP Application No. 04759018.7, filed on Mar. 29, 2004, twenty-nine pages.
Letter dated Jul. 6, 2011, Opposition to European Patent EP Application No. 04759018.7, Representative Muller Fottner Steinecke further to Opposition Brief, sixty-three pages.
European Patent Office Communication mailed Nov. 25, 2011, for EP Application No. 04759018.7, filed Mar. 29, 2004, three pages.
European Patent Office Communication mailed on Jan. 25, 2012, for EP Patent Application No. 04759018.7, filed on Mar. 29, 2004, twelve pages.
European Patent Office Communication mailed on Mar. 1, 2012, for EP Patent Application No. 04759018.7, filed on Mar. 29, 2004, three pages.
Doutrelepont, J.M. et al. (1991). "Hyper IgE in Stimulatory Graft-*versus*-Host Disease: Role of Interleukin-4," *Clin. Exp. Immunol.* 83:133-136.

\* cited by examiner

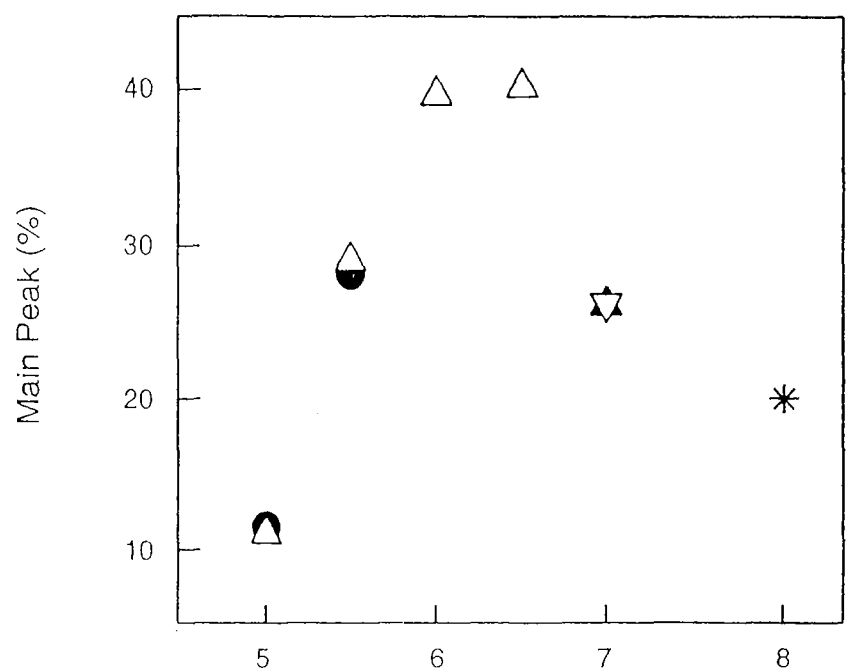
FIG._1
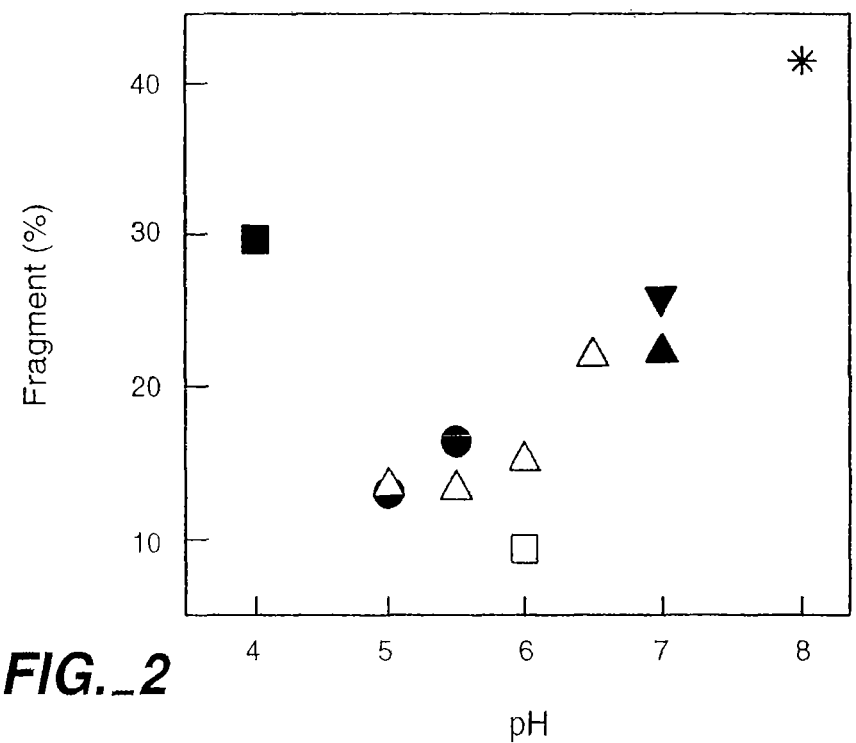
FIG._2

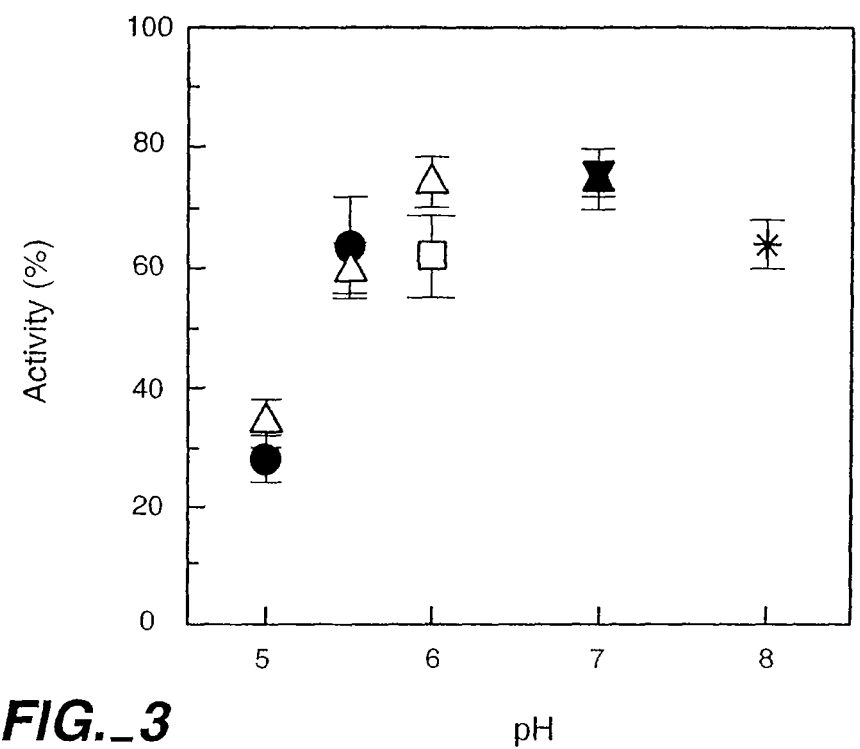
FIG._3
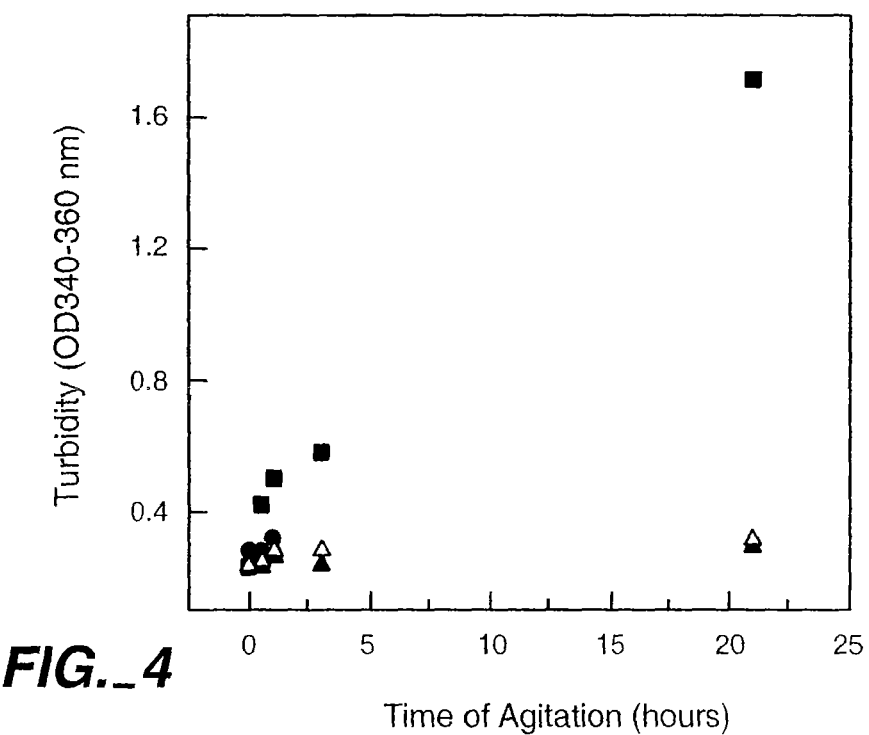
FIG._4

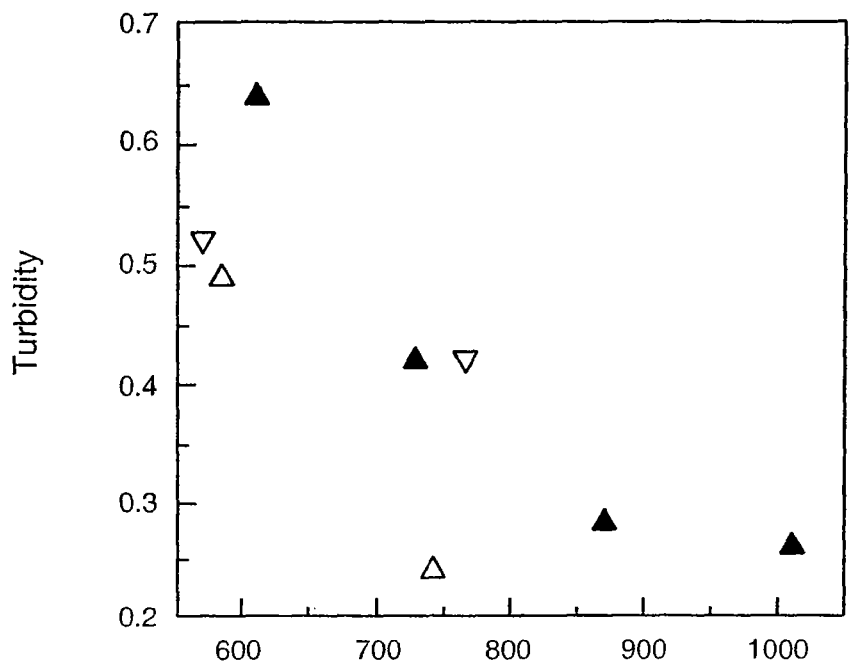
FIG._5
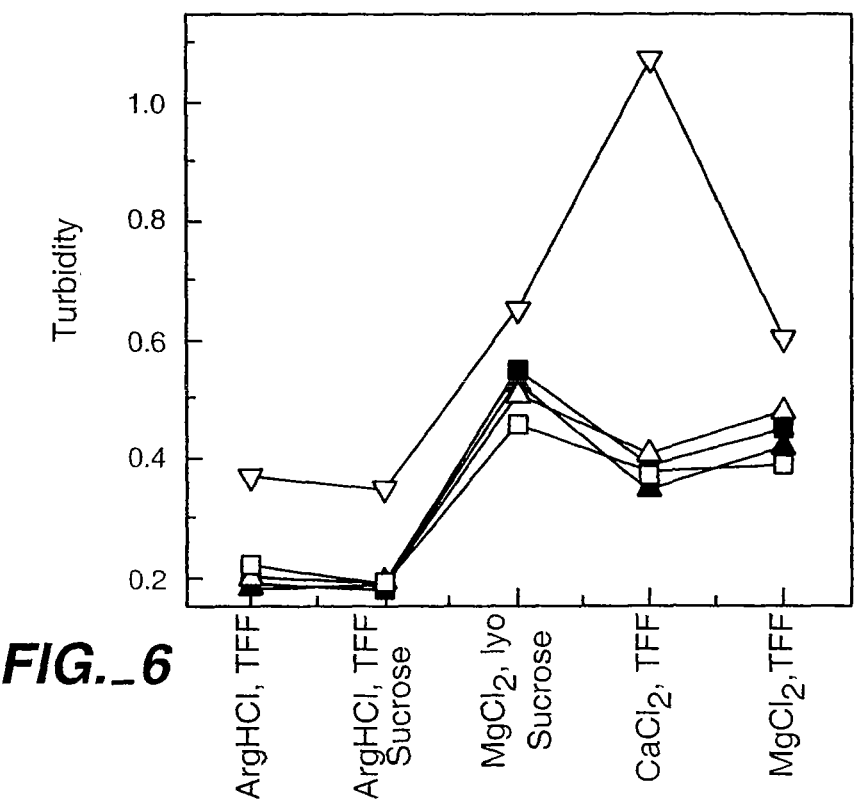
FIG._6

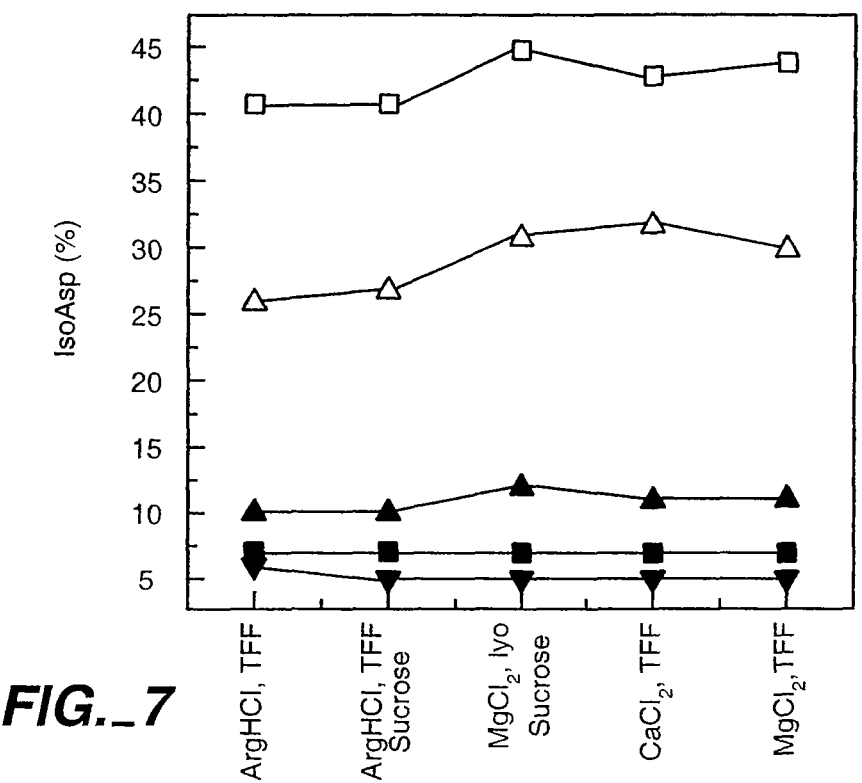
FIG._7
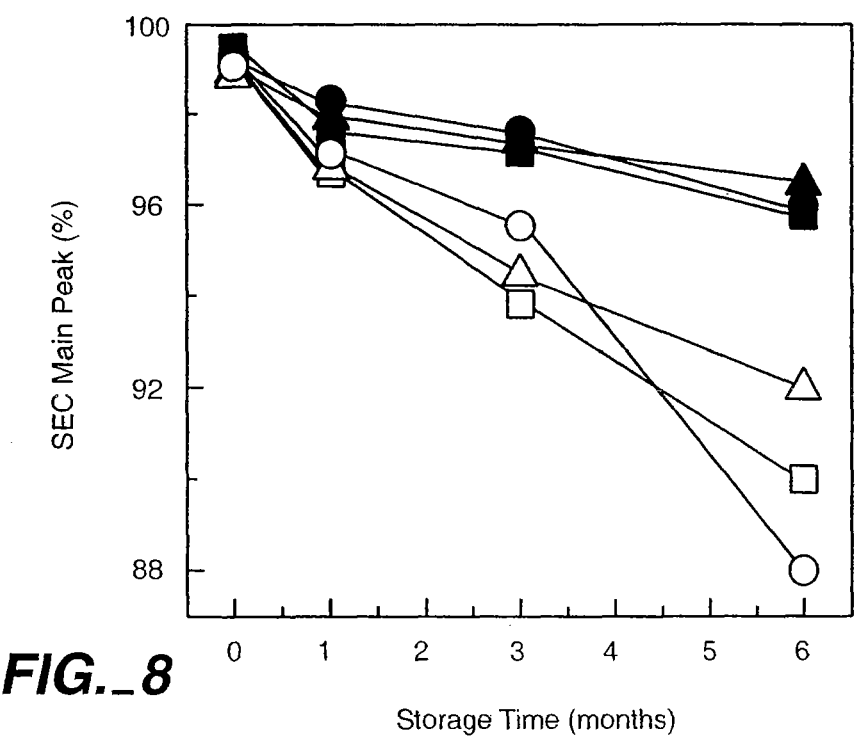
FIG._8

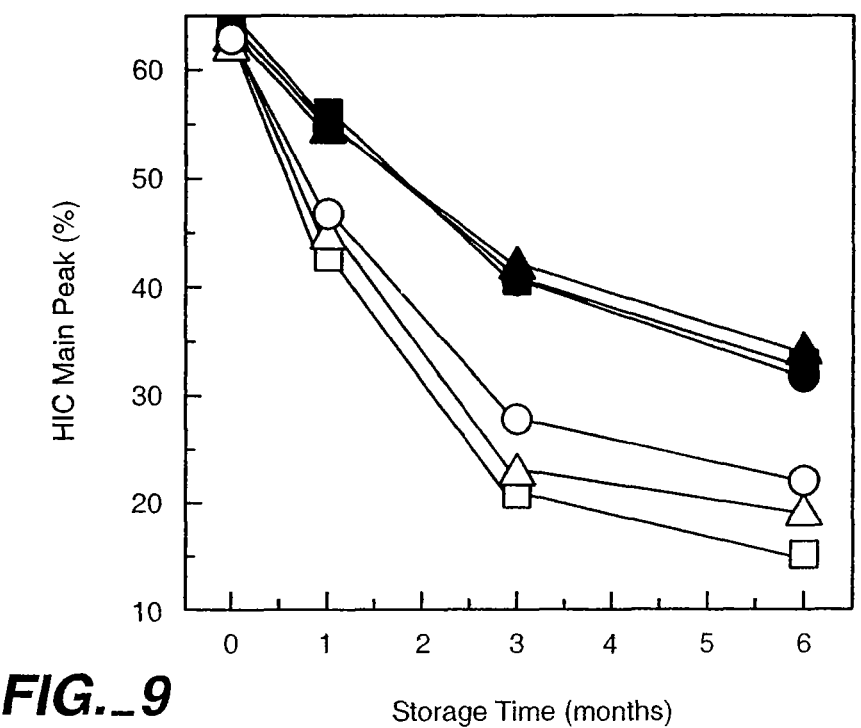
FIG._9

Anti-IgE Antibodies: Light Chain (V$_L$ and C$_L$ Domains)

```
              10         20         30         40         50         60         70         80
E25     DIQLTQSPSS LSASVGDRVT ITC[RASQSVD YDGDSYMN]WY QQKPGKAPKL LIY[AASYLES] GVPSRFSGSG SGTDFTLTIS
E26     DIQLTQSPSS LSASVGDRVT ITC[RASKPVD GEGDSYLN]WY QQKPGKAPKL LIY[AASYLES] GVPSRFSGSG SGTDFTLTIS
Hu-901  DIQLTQSPGT LSLSPGERAT LSC RASQSIG TNIH----- WY QQKPGQAPRL LIK VASESIS GIPSRFSGSG SGTDFTLTIS
                                            C_L starts
              90        100        110
E25     SLQPEDFATY YC[QQSHEDPY T]FGQGTKVEI KRT VAAPSVFIFPPSDEQLKSGTASVVCLLNNFYPREAKVQWKVDNALQSGNSQESVTEQD
E26     SLQPEDFATY YC[QQSHEDPY T]FGQGTKVEI KRT VAAPSVFIFPPSDEQLKSGTASVVCLLNNFYPREAKVQWKVDNALQSGNSQESVTEQD
Hu-901  RLEPEDFAMY YC QQSDSWPT T FGQGTKVEI KRT VAAPSVFIFPPSDEQLKSGTASVVCLLNNFYPREAKVQWKVDNALQSGNSQESVTEQD E25     SKDSTYSLSSTLTLSKADYEKHKVYACEVTHQGLSSPVTKSFNRGEC
E26     SKDSTYSLSSTLTLSKADYEKHKVYACEVTHQGLSSPVTKSFNRGEC
Hu-901  SKDSTYSLSSTLTLSKADYEKHKVYACEVTHQGLSSPVTKSFNRGEC
```

FIG._10A

Anti-IgE Antibodies: Heavy Chain ($V_H$ and $C_H$ Domains)

```
              10         20         30         40         50 a        60           70         80         90
E25   EVQLVESGGG LVQPGGSLRL SCAVSGYSIT S[GYSWNW]IRQ APGKGLEWVA [SITYDGSTNY NPSVKG]RITI SRDDSKNTFY LQMNSLRAED
E26   EVQLVESGGG LVQPGGSLRL SCAVSGYSIT S[GYSWNW]IRQ APGKGLEWVA [SITYDGSTNY NPSVKG]RITI SRDDSKNTFY LQMNSLRAED
Hu-901 QVQLVQSGAE VKKPGASVKV SCKASGYTF- S MNLEW VRQ APGQGLEWMG EISPGTFTTNY NEKFKA RATF TADTSTNTAY MELSSLRSED 100        110ab       120 C_H starts
E25   TAVYYCAR[GS HYFGHWHFAV] WGQGTLVTVSS ASTKGPSVF PLAPSSKSTSG GTAALGCLVKDYF PEPVTVSWNSGALTSGVHTFPAVLQSSGLYSLSS
E26   TAVYYCAR[GS HYFGHWHFAV] WGQGTLVTVSS ASTKGPSVF PLAPSSKSTSG GTAALGCLVKDYF PEPVTVSWNSGALTSGVHTFPAVLQSSGLYSLSS
Hu-901 TAVYYCAR FS HFSGSNYDYFDY WGQGTLVTVSS ASTKGPSVF PLAPSSKSTSG GTAALGCLVKDYF PEPVTVSWNSGALTSGVHTFPAVLQSSGLYSLSS E25   VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYDGVE
E26   VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYDGVE
Hu-901 VVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYDGVE E25   VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE
E26   VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWE
Hu-901 VHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWE E25   SNGQPENNYKTTPPVLDSDGSFFLYSKLTVDKSRWQQGNVFSCSVMHEALHNHYTQKSLSLSPGK
E26   SNGQPENNYKTTPPVLDSDGSFFLYSKLTVDKSRWQQGNVFSCSVMHEALHNHYTQKSLSLSPGK
Hu-901 SNGQPENNYKTTPPVLDSDGSFFLYSKLTVDKSRWQQGNVFSCSVMHEALHNHYTQKSLSLSPGK
```

FIG. _10B

SEQUENCE LISTING

<160> NUMBER OF SEQ ID NOS: 6

<210> SEQ ID NO 1
<211> LENGTH: 218
<212> TYPE: PRT
<213> ORGANISM: Artificial sequence
<220> FEATURE:
<223> OTHER INFORMATION: E25, light chain

<400> SEQUENCE: 1

```
Asp Ile Gln Leu Thr Gln Ser Pro Ser Leu Ser Ala Ser Val
  1               5                  10                  15

Gly Asp Arg Val Thr Ile Thr Cys Arg Ala Ser Gln Ser Val Asp
                 20                  25                  30

Tyr Asp Gly Asp Ser Tyr Met Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser His Glu Asp Pro Tyr Thr Phe Gly Gln Gly
                 95                 100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215
```

<210> SEQ ID NO 2
<211> LENGTH: 218
<212> TYPE: PRT
<213> ORGANISM: Artificial sequence
<220> FEATURE:
<223> OTHER INFORMATION: E26, light chain

<400> SEQUENCE: 2

```
Asp Ile Gln Leu Thr Gln Ser Pro Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60
```

```
Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
             80                  85                  90

Tyr Cys Gln Gln Ser His Glu Asp Pro Tyr Thr Phe Gly Gln Gly
             95                 100                 105

Thr Lys Val Glu Ile Lys Arg Thr Val Ala Ala Pro Ser Val Phe
            110                 115                 120

Ile Phe Pro Pro Ser Asp Glu Gln Leu Lys Ser Gly Thr Ala Ser
            125                 130                 135

Val Val Cys Leu Leu Asn Asn Phe Tyr Pro Arg Glu Ala Lys Val
            140                 145                 150

Gln Trp Lys Val Asp Asn Ala Leu Gln Ser Gly Asn Ser Gln Glu
            155                 160                 165

Ser Val Thr Glu Gln Asp Ser Lys Asp Ser Thr Tyr Ser Leu Ser
            170                 175                 180

Ser Thr Leu Thr Leu Ser Lys Ala Asp Tyr Glu Lys His Lys Val
            185                 190                 195

Tyr Ala Cys Glu Val Thr His Gln Gly Leu Ser Ser Pro Val Thr
            200                 205                 210

Lys Ser Phe Asn Arg Gly Glu Cys
            215

<210> SEQ ID NO 3
<211> LENGTH: 214
<212> TYPE: PRT
<213> ORGANISM: Artificial sequence
<220> FEATURE:
<223> OTHER INFORMATION: Hu-901, light chain

<400> SEQUENCE: 3

Asp Ile Leu Leu Thr Gln Ser Pro Gly Thr Leu Ser Leu Ser Pro
  1               5                  10                  15

Gly Glu Arg Ala Thr Leu Ser Cys Arg Ala Ser Gln Ser Ile Gly
             20                  25                  30

Thr Asn Ile His Trp Tyr Gln Gln Lys Pro Gly Gln Ala Pro Arg
             35                  40                  45

Leu Leu Ile Lys Tyr Ala Ser Glu Ser Ile Ser Gly Ile Pro Ser
             50                  55                  60

Arg Phe Ser Gly Ser Gly Ser Gly Thr Asp Phe Thr Leu Thr Ile
             65                  70                  75

Ser Arg Leu Glu Pro Glu Asp Phe Ala Met Tyr Tyr Cys Gln Gln
             80                  85                  90

Ser Asp Ser Trp Pro Thr Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180
```

-continued

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 4
<211> LENGTH: 451
<212> TYPE: PRT
<213> ORGANISM: Artificial sequence
<220> FEATURE:
<223> OTHER INFORMATION: E25, heavy chain

<400> SEQUENCE: 4

Glu Val Gln Leu Val Glu Ser Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln

```
                    305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys

<210> SEQ ID NO 5
<211> LENGTH: 451
<212> TYPE: PRT
<213> ORGANISM: Artificial sequence
<220> FEATURE:
<223> OTHER INFORMATION: E26, heavy chain

<400> SEQUENCE: 5

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195
```

```
Ser Leu Gly Thr Gln Thr Tyr Ile Cys Asn Val Asn His Lys Pro
            200                 205                 210

Ser Asn Thr Lys Val Asp Lys Lys Val Glu Pro Lys Ser Cys Asp
            215                 220                 225

Lys Thr His Thr Cys Pro Pro Cys Pro Ala Pro Glu Leu Leu Gly
            230                 235                 240

Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln
            305                 310                 315

Asp Trp Leu Asn Gly Lys Glu Tyr Lys Cys Lys Val Ser Asn Lys
            320                 325                 330

Ala Leu Pro Ala Pro Ile Glu Lys Thr Ile Ser Lys Ala Lys Gly
            335                 340                 345

Gln Pro Arg Glu Pro Gln Val Tyr Thr Leu Pro Pro Ser Arg Glu
            350                 355                 360

Glu Met Thr Lys Asn Gln Val Ser Leu Thr Cys Leu Val Lys Gly
            365                 370                 375

Phe Tyr Pro Ser Asp Ile Ala Val Glu Trp Glu Ser Asn Gly Gln
            380                 385                 390

Pro Glu Asn Asn Tyr Lys Thr Thr Pro Pro Val Leu Asp Ser Asp
            395                 400                 405

Gly Ser Phe Phe Leu Tyr Ser Lys Leu Thr Val Asp Lys Ser Arg
            410                 415                 420

Trp Gln Gln Gly Asn Val Phe Ser Cys Ser Val Met His Glu Ala
            425                 430                 435

Leu His Asn His Tyr Thr Gln Lys Ser Leu Ser Leu Ser Pro Gly
            440                 445                 450

Lys

<210> SEQ ID NO 6
<211> LENGTH: 453
<212> TYPE: PRT
<213> ORGANISM: Artificial sequence
<220> FEATURE:
<223> OTHER INFORMATION: Hu-901, heavy chain

<400> SEQUENCE: 6

Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Ser
            20                  25                  30

Met Tyr Trp Leu Glu Trp Val Arg Gln Ala Pro Gly His Gly Leu
            35                  40                  45

Glu Trp Val Gly Glu Ile Ser Pro Gly Thr Phe Thr Thr Asn Tyr
            50                  55                  60

Asn Glu Lys Phe Lys Ala Arg Ala Thr Phe Thr Ala Asp Thr Ser
            65                  70                  75
```

-continued

```
Thr Asn Thr Ala Tyr Met Glu Leu Ser Ser Leu Arg Ser Glu Asp
             80                  85                  90

Thr Ala Val Tyr Tyr Cys Ala Arg Phe Ser His Phe Ser Gly Ser
         95                 100                 105

Asn Tyr Asp Tyr Phe Asp Tyr Trp Gly Gln Gly Thr Leu Val Thr
            110                 115                 120

Val Ser Ser Ala Ser Thr Lys Gly Pro Ser Val Phe Pro Leu Ala
            125                 130                 135

Pro Ser Ser Lys Ser Thr Ser Gly Gly Thr Ala Ala Leu Gly Cys
            140                 145                 150

Leu Val Lys Asp Tyr Phe Pro Glu Pro Val Thr Val Ser Trp Asn
            155                 160                 165

Ser Gly Ala Leu Thr Ser Gly Val His Thr Phe Pro Ala Val Leu
            170                 175                 180

Gln Ser Ser Gly Leu Tyr Ser Leu Ser Ser Val Val Thr Val Pro
            185                 190                 195

Ser Ser Ser Leu Gly Thr Gln Thr Tyr Ile Cys Asn Val Asn His
            200                 205                 210

Lys Pro Ser Asn Thr Lys Val Asp Lys Lys Val Glu Pro Lys Ser
            215                 220                 225

Cys Asp Lys Thr His Thr Cys Pro Pro Cys Pro Ala Pro Glu Leu
            230                 235                 240

Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu
            305                 310                 315

His Gln Asp Trp Leu Asn Gly Lys Glu Tyr Lys Cys Lys Val Ser
            320                 325                 330

Asn Lys Ala Leu Pro Ala Pro Ile Glu Lys Thr Ile Ser Lys Ala
            335                 340                 345

Lys Gly Gln Pro Arg Glu Pro Gln Val Tyr Thr Leu Pro Pro Ser
            350                 355                 360

Arg Asp Glu Leu Thr Lys Asn Gln Val Ser Leu Thr Cys Leu Val
            365                 370                 375

Lys Gly Phe Tyr Pro Ser Asp Ile Ala Val Glu Trp Glu Ser Asn
            380                 385                 390

Gly Gln Pro Glu Asn Asn Tyr Lys Thr Thr Pro Pro Val Leu Asp
            395                 400                 405

Ser Asp Gly Ser Phe Phe Leu Tyr Ser Lys Leu Thr Val Asp Lys
            410                 415                 420

Ser Arg Trp Gln Gln Gly Asn Val Phe Ser Cys Ser Val Met His
            425                 430                 435

Glu Ala Leu His Asn His Tyr Thr Gln Lys Ser Leu Ser Leu Ser
            440                 445                 450

Pro Gly Lys
```

HIGH CONCENTRATION ANTIBODY AND PROTEIN FORMULATIONS

This application is a continuation application of U.S. patent application Ser. No. 12/197,005, filed Aug. 22, 2008, which is a continuation application of U.S. patent application Ser. No. 10/813,483, filed Mar. 29, 2004, which is a non-provisional application claiming priority to provisional application Ser. No. 60/460,659, filed Apr. 4, 2003, the contents of which are incorporated herein by reference in their entirety.

BACKGROUND OF THE INVENTION

1. Field of the Invention

This invention pertains to highly concentrated formulations of antibodies, which are particularly suitable for subcutaneous administration. The invention further provides stable, highly concentrated (e.g., ≥100 mg/ml protein) liquid formulations.

2. Description of the Related Art

There is a significant demand for highly concentrated liquid antibody formulations. However, highly concentrated protein formulations pose several problems. One problem is instability due to the formation of particulates. With reconstituted lyophilized preparations to generate liquid formulations, this problem has been addressed through the use of surfactants (e.g., a polysorbate), but surfactants are unsuitable for liquid formulations, because they render further processing difficult. Moreover, surfactants further do not reduce the increased viscosity caused as a result of numerous intermolecular interactions from the macromolecular nature of antibodies.

Although surfactants have been shown to significantly reduce the degree of particulate formation of proteins, they do not address the problem of increased viscosity that makes difficult the manipulation and administration of concentrated antibody formulations. Antibodies tend to form viscous solutions at high concentration because of their macromolecular nature and potential for intermolecular interactions. Moreover, pharmaceutically acceptable sugars are often used in large amounts as stabilizers. Such sugars can enhance the intermolecular interactions, thereby increasing the viscosity of the formulation. Highly viscous formulations are difficult to manufacture, draw into a syringe and inject subcutaneously. The use of force in manipulating the viscous formulations leads to excessive frothing, which can lead to denaturation and inactivation of active biologics. Satisfactory solution of this problem is lacking.

While the prior art indicates numerous example of excipients that can be suitably employed to create pharmaceutical formulations, very few proteins have been successfully formulated above 100 mg/ml, or have techniques for doing so been described.

Applicants have discovered that Arginine, specifically Arginine-HCl is particularly suited for highly concentrated liquid protein or antibody formulations.

Stable isotonic lyophilized protein formulations are disclosed in PCT publication WO 97/04801, published on Feb. 13, 1997, the entire disclosure of which is hereby expressly incorporated by reference. The disclosed lyophilized formulations can be reconstituted to generate high protein-concentration liquid formulations without apparent loss of stability. However, the potential issues associated with the high viscosity of the reconstituted formulations are not addressed. Protein aggregation has been reduced previously through the addition of sugars, but doing so can dramatically increase the viscosity and osmolarity, thereby rendering processing and use impractical.

Applicants co-pending application U.S. Ser. No. 09/971,511, filed Oct. 4, 2001 discloses high protein concentration, but low viscosity formulations achieved: 1) through low pH (about 4.0 to 5.3); 2) high pH (about 6.5 to 12.0), or 3) increasing the total ionic strength of the formulation by the addition of salts or buffers. However, while increased ionic strength does decrease the viscosity of the formulation (such as with NaCl), it may also result in increased turbidity of the solution, which is often associated with the formation of protein particles (e.g., aggregation). Thus an optimal high concentration protein formulation must overcome challenges of stability, viscosity, osmolarity and turbidity.

SUMMARY OF THE INVENTION

The present invention concerns highly concentrated protein or antibody formulations that are stable, and of low viscosity and turbidity.

In particular, the present invention concerns highly concentrated antibody formulations of low turbidity comprising protein or antibody (100-260 mg/ml), histidine (10-100 mM), arginine-HCl (50-200 mM) and polysorbate (0.01%-0.1%), having a pH of 5.5-7.0, a viscosity of 50 cs or less and osmolarity from 200 mOsm/kg-450 mOsm/kg. Alternatively, the protein or antibody in the formulations can range from 120-260 mg/ml, alternatively 150-260 mg/ml, alternatively 180-260 mg/ml, alternatively 200-260 mg/ml protein or antibody. Alternatively the osmolarity ranges from 250 mOsm/kg-350 mOsm/kg. Alternatively, the concentration of arginine-HCl ranges from 100-200 mM, alternatively 150-200 mM, alternatively 180-200 mM.

Alternatively, the present invention concerns a highly concentrated antibody formulations of low turbidity comprising antibody (40-150 mg/ml), histidine (10-100 mM), sugar (e.g., trehalose or sucrose, 20-350 mM) and polysorbate (0.01%-0.1%).

In a particular embodiment, the invention provides a formulation containing high concentrations of large molecular weight proteins, such as antibodies or immunoglobulins. The antibodies may, for example, be antibodies directed against a particular predetermined antigen. In a specific aspect, the antigen is IgE (e.g., rhuMAbE-25, rhuMAbE-26 described in U.S. Pat. No. 6,329,509 and WO 99/01556). Alternatively, the anti-IgE antibody can be CGP-5101 (Hu-901) described in Come et al., *J. Clin. Invest.* 99(5): 879-887 (1997), WO92/17207, and ATTC Deposit Nos. BRL-10706 and 11130, 11131, 11132, 11133. Alternatively, the antigen may include: the CD proteins CD3, CD4, CD8, CD19, CD20, CD34 and CD40; members of the HER receptor family such as EGF receptor, HER2, HER3 or HER4 receptor; 2C4, 4D5, PSCA, LDP-2, cell adhesion molecules such as LFA-1, Mac1, p150, 95, VLA-4, ICAM-1, VCAM and αv/β3 integrin including the α- and β-subunits thereof (e.g., anti-CD11a, anti-CD18 or anti-CD11b antibodies); growth factors such as VEGF; blood group antigens; flk2/flt3 receptor; obesity (OB) receptor; mpl receptor, CTLA-4, and protein C.

The formulations of the present invention may be pharmaceutical formulations. In a specific aspect, the formulation is delivered subcutaneously.

In yet another embodiment, the invention provides a method for the treatment, prophylactic or therapeutic, of a disorder treatable by the protein or antibody formulated, comprising administering the formulations disclosed herein comprising a therapeutically effective amount of the protein or antibody. Such formulations are particularly useful for subcutaneous administration. In a specific aspect, the disorder is an IgE-mediated disorder. In yet a further specific aspect, the IgE-mediated disorder is allergic rhinitis, asthma (e.g., allergic asthma and non-allergic asthma), atopic dermatitis, allergic gastroenteropathy, hypersensitivity (e.g., analphylaxis, urticaria, food allergies etc.), allergic bronchopulmonary aspergillosis, parasitic diseases, interstitial cystitis, hyper-IgE syndrome, ataxia-telangiectasia, Wiskott-Aldrich syndrome, thymic alymphoplasia, IgE myeloma and graft-versus-host reaction.

In yet another embodiment, the invention provides an article of manufacture comprising a container enclosing a formulation disclosed herein. In one aspect, the article of manufacture is pre-filled syringe. In yet another specific aspect, the pre-filled syringe is further containing within an injection device. In yet another specific aspect, the injection device is an auto-injector.

BRIEF DESCRIPTION OF THE DRAWINGS

FIG. 1. Hydrophobic interaction chromatography of a pepsin digested anti-IgE monoclonal antibody. Samples were formulated at different pH and buffers: (●) 20 mM Acetate, (Δ) 20 mM Succinate, (▲) 20 mM $Na_2HPO_4$, (▽) 20 mM $K_2PO_4$ and (*) 20 mM Tris buffer. The samples were stored at 30° C. for 6 months.

FIG. 2. Size exclusion chromatography of an anti-IgE monoclonal antibody stored at 40° C. for 6 months. Samples were formulated at different pH and buffers: (■) 20 mM Glutamate, (●) 20 mM Acetate, (Δ) 20 mM Succinate, (□) 20 mM Histidine, (▲) 20 mM $Na_2HPO_4$, (▽) 20 mM $K_2PO_4$ and (*) 20 mM Tris buffer.

FIG. 3. Activity of an anti-IgE monoclonal antibody stored at 30° C. for 6 months. Samples were formulated at different pH and buffers: (●) 20 mM Acetate, (Δ) 20 mM Succinate, (□) 20 mM Histidine, (▲) 20 mM $Na_2HPO_4$, (▽) 20 mM $K_2PO_4$ and (*) 20 mM Tris buffer.

FIG. 4. Effects of Polysorbate 20 on turbidity of the stressed anti-IgE monoclonal antibody. Samples contain 100 mg/ml antibody, 20 mM Succinate, 192 mM Trehalose and various amounts of polysorbate 20 at pH 6.0. The polysorbate concentrations are (■) 0, (▲) 0.01%, (●) 0.02% and (Δ) 0.05%.

FIG. 5. Turbidity of an anti-IgE monoclonal antibody at ~150 mg/ml with different excipients (▲) $CaCl_2$, (▽) $MgCl_2$ and (Δ) Arginine-HCl FIG. 6. Turbidity of anti-IgE monoclonal antibody at –150 mg/ml with various excipients. The samples were stored at (▲) –70° C., (■) 2-8° C., (Δ) 15° C., (□) 30° C. and (▽) 40° C.

FIG. 7. Hydrophobic interaction chromatography analyses of papain digested anti-IgE monoclonal antibody. Samples were formulated at –150 mg/ml with various of excipients and stored at (▽) –70° C., (■) 2-8° C., (▲) 15° C., (Δ) 30° C. and (□) 40° C.

FIG. 8. Size exclusion chromatography of anti-IgE monoclonal antibody at ~150 mg/ml in (■) 200 mM arginine-HCl, 23 mM histidine, pH 6.0 (▲) 182 mM arginine-HCl, 20 mM histidine, pH 6.0 (●) 182 mM arginine-HCl, 20 mM histidine, 91 mM sucrose, pH 6.0 (□) 50 mM $MgCl_2$, 27 mg/ml trehalose, 0.01% acetate, (Δ) 50 mM $MgCl_2$, 30 mM $MgAc_2$, 0.01% acetate, and (○) 50 mM $MgCl_2$, 45 mM $MgAc_2$, 0.01% acetate. Samples were stored at 30° C. for 6 months.

FIG. 9. Hydrophobic interaction chromatography analyses of papain digested anti-IgE monoclonal antibody. The samples show were formulated in (■) 200 mM arginine-HCl, 23 mM histidine, (▲) 182 mM arginine-HCl, 20 mM histidine, (●) 182 mM arginine-HCl, 20 mM histidine, 91 mM sucrose, (□) 50 mM $MgCl_2$, 27 mg/ml trehalose, 0.01% acetate, (Δ) 50 mM $MgCl_2$, 30 mM $MgAc_2$, 0.01% acetate and (○) 50 mM $MgCl_2$, 45 mM $MgAc_2$, 0.01% acetate. Samples were stored at 30° C. for 6 months.

FIG. 10. Shows a comparison of the full-length sequences both variable and constant chains) of the anti-IgE antibodies E25, E26 and Hu-901. The CDR regions of Hu-901 is shown by underline. For E25 and E26, the CDR regions as defined by Chothia are shown in boldface, while the CDR region as defined by Kabat are delineated with brackets. FIG. 10A shows the light chain sequences of E25, E26 and Hu-901 (SEQ ID NOS:1-3), while FIG. 10B shows the heavy chain sequences of E25, E26 and Hu-901 (SEQ ID NOS:4-6).

DETAILED DESCRIPTION OF THE PREFERRED EMBODIMENT

I. Definitions

By "protein" is meant a sequence of amino acids for which the chain length is sufficient to produce the higher levels of tertiary and/or quaternary structure. Thus, proteins are distinguished from "peptides" which are also amino acid-based molecules that do not have such structure. Typically, a protein for use herein will have a molecular weight of at least about 15-20 kD, preferably at least about 20 kD.

Examples of proteins encompassed within the definition herein include mammalian proteins, such as, e.g., growth hormone, including human growth hormone and bovine growth hormone; growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA, e.g., Activase®, TNKase®, Retevase®); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins;

homing receptors; addressins; regulatory proteins; immunoadhesins; antibodies; and biologically active fragments or variants of any of the above-listed polypeptides.

The protein which is formulated is preferably essentially pure and desirably essentially homogeneous (i.e. free from contaminating proteins). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

In certain embodiments, the protein is an antibody. The antibody may bind to any of the above-mentioned molecules, for example. Exemplary molecular targets for antibodies encompassed by the present invention include IgE, the CD proteins CD3, CD4, CD8, CD19, CD20, CD34 and CD40; members of the HER receptor family such as EGF receptor, HER2, HER3 or HER4 receptor; 2c4, 4D5, PSCA, LDP-2, cell adhesion molecules such as LFA-1, Mac1, p150, 95, VLA-4, ICAM-1, VCAM and αv/β3 integrin including the α- and β-subunits thereof (e.g., anti-CD11a, anti-CD18 or anti-CD11b antibodies); growth factors such as VEGF; blood group antigens; flk2/flt3 receptor; obesity (OB) receptor; mpl receptor, CTLA-4, and protein C.

Additional antibodies that can be made with the formulation described herein include those that specifically bind to the antigenic targets disclosed in the following patent applications: U.S. Ser. No. 10/177,488, filed 19 Jun. 2002; U.S. Ser. No. 09/888,257, filed 22 Jun. 2001; U.S. Ser. No. 09/929,769, filed 14 Aug. 2001; U.S. Ser. No. 09/938,418, filed 23 Aug. 2001; U.S. Ser. No. 10/241,220, filed 11 Sep. 2002; U.S. Ser. No. 10/331,496, filed 30 Dec. 2002; U.S. Ser. No. 10/125,166, filed 17 Apr. 2002; U.S. Ser. No. 10/127,966, filed 23 Apr. 2002; U.S. Ser. No. 10/272,051, filed 16 Oct. 2002; U.S. Ser. No. 60/299,500, filed 20 Jun. 2001; U.S. Ser. No. 60/300,880, filed 25 Jun. 2001; U.S. Ser. No. 60/301,880, filed 29 Jun. 2001; U.S. Ser. No. 60/304,813, filed 11 Jul. 2001; U.S. Ser. No. 60/312,312, filed 13 Aug. 2001; U.S. Ser. No. 60/314,280, filed 22 Aug. 2001; U.S. Ser. No. 60/323,268, filed 18 Sep. 2001; U.S. Ser. No. 60/339,227, filed 19 Oct. 2001; U.S. Ser. No. 60/336,827, filed 7 Nov. 2001; U.S. Ser. No. 60/331,906, filed 20 Nov. 2001; U.S. Ser. No. 60/354,444, filed 2 Jan. 2002; U.S. Ser. No. 60/351,885, filed 25 Jan. 2002; U.S. Ser. No. 60/360,066, filed 25 Feb. 2002; U.S. Ser. No. 60/362,004, filed 5 Mar. 2002; U.S. Ser. No. 60/366,869, filed 20 Mar. 2002; U.S. Ser. No. 60/366,284, filed 21 Mar. 2002; U.S. Ser. No. 60/368,679, filed 28 Mar. 2002; U.S. Ser. No. 60/369,724, filed 3 Apr. 2002; U.S. Ser. No. 60/373,160, filed 16 Apr. 2002; U.S. Ser. No. 60/378,885, filed 8 May 2002; U.S. Ser. No. 60/404,809, filed 19 Aug. 2002; U.S. Ser. No. 60/405,645, filed 21 Aug. 2002; U.S. Ser. No. 60/407,087, filed 29 Aug. 2002; U.S. Ser. No. 60/413,192, filed 23 Sep. 2002; U.S. Ser. No. 60/419,008, filed 15 Oct. 2002; U.S. Ser. No. 60/426,847, filed 15 Nov. 2002; U.S. Ser. No. 60/431,250, filed 6 Dec. 2002; U.S. Ser. No. 60/437,344, filed 31 Dec. 2002, U.S. Ser. No. 60/414,971, filed 2 Oct. 2002, U.S. Ser. No. 60/418,988, filed 18 Oct. 2002 and 60/445,396, filed 5 Feb. 2003.

The term "antibody" as used wherein includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Ten and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and μ classes are further divided into subclasses on the basis of relatively minor differences in the CH sequence and function, e.g., humans express the following subclasses: IgG1, IgG2, IgG3, IgG4, IgA1 and IgA2.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, the V regions consist of relatively invariant stretches called framework regions (FRs) of about 15-30 amino acid residues separated by shorter regions of extreme variability called "hypervariable regions" or sometimes "complementarity determining regions" (CDRs) that are each approximately 9-12 amino acid residues in length. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen binding site of antibodies (see Kabat et al., *Sequences of Proteins of Immunological Interest*, 5th Ed. Public Health Service, National Institutes of Health, Bethesda, Md. (1991). The constant domains are not involved directly in binding an antibody to an antigen, but exhibit various effector functions, such as participation of the antibody dependent cellular cytotoxicity (ADCC).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i.e., Kabat et al., *Sequences of Proteins of Immunological Interest* (National Institute of Health, Bethesda, Miss. 1991); and (2) An approach based on crystallographic studies of antigen-antibody complexes (Chothia, C. et al., *J. Mol. Biol.* 196: 901-917 (1987)). However, to the extent that two residue identification techniques define regions of overlapping, but not identical regions, they can be combined to define a hybrid CDR.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primitized" antibodies comprising variable domain antigen-binding sequences derived from a non-human primate (e.g., Old World Monkey, Ape etc.) and human contant region sequences.

An "intact" antibody is one which comprises an antigen-binding site as well as a CL and at least the heavy chain domains, $C_H1$, $C_H2$ and $C_H3$. The constant domains may be native sequence constant domains (e.g., human native sebquence constant domains) or amino acid sequence variants thereof. Preferably, the intact antibody has one or more effector functions.

An "antibody fragment" comprises a portion of an intact antibody, preferably the antigen binding and/or the variable region of the intact antibody. Examples of antibody fragments include Fab, Fab', $F(ab')_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervarible loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies,* vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The term "solid phase" describes a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromotography column). This term also includes a discontinuous solid phase of discrete particles, such as those described in U.S. Pat. No. 4,275,149.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992).

A "species-dependent antibody", e.g. a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, alternatively no more than about $1\times. 10^{-8}$ M, alternatively no more than about $1\times10^{-9}$ M) but has a binding affinity for a homologue of the antigen from a second non-human mammalian species which is at least about 50 fold, at least about 500 fold, or at least about 1000 fold, waker than it binding affinity for the non-human antigen. The species-dependent antibody can be of any of the various types of antibodies as defined above, but preferably is a humanized or human antibody.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ACDD assay, such as that described in U.S. Pat. No. 5,500,362 or U.S. Pat. No. 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ Primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITEM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

"Complement dependent cytotoxicity" of "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed.

"Isolated" when used to describe the various polypeptides and antibodies disclosed herein, means a polypeptide or antibody that has been identified, separated and/or recovered from a component of its production environment. Preferably, the isolated polypeptide is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated polypeptide or antibody will be prepared by at least one purification step.

An "isolated" nucleic acid molecule encoding the polypeptides and antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "epitope tagged" when used herein refers to a chimeric polypeptide comprising a polypeptide or antibody described herein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein throughout. The reconstituted formulation is suitable for administration (e.g. parenteral administration) to a patient to be treated with the protein of interest and, in certain embodiments of the invention, may be one which is suitable for subcutaneous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

A "reconstituted" formulation is one which has been prepared by dissolving a lyophilized protein formulation in a diluent such that the protein is dispersed in the reconstituted formulation. The reconstituted formulation is suitable for administration (e.g. parenteral administration) to a patient to be treated with the protein of interest and, in certain embodiments of the invention, may be one which is suitable for subcutaneous administration.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cyloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases were are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amine, substituted amines, cyclic amines and basic ion exchange resins, [e.g., N(R')$_4^+$ (where R' is independently H or C$_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and or salts include histidine, succinate and acetate.

A "lyoprotectant" is a molecule which, when combined with a protein of interest, significantly prevents or reduces chemical and/or physical instability of the protein upon lyophilization and subsequent storage. Exemplary lyoprotectants include sugars and their corresponding sugar alchohols; an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred lyoprotectant are the non-reducing sugars trehalose or sucrose.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In preparing the reduced viscosity formulations of the invention, care should be taken using the above enumerated excipients as well as other additives, especially when added at high concentration, so as to not increase the viscosity of the formulation.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols includes: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose.

Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and allergies.

A "therapeutically effective amount" is at least the minimum concentration required to effect a measurable improvement or prevention of a particular disorder. Therapeutically effective amounts of known proteins are well known in the art, while the effective amounts of proteins hereinafter discovered may be determined by standard techniques which are well within the skill of a skilled artisan, such as an ordinary physician.

"Viscosity" as used herein may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. If one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density:

Absolute Viscosity=Kinematic Viscosity×Density

The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

An "antihistamine" as used herein is an agent that antagonizes the physiological effect of histamine. The binding of histamine to its receptors, $H_1$ and $H_2$ results in the characteristic allergic symptoms and effects or itching, redness, swelling etc. Many antihistamines act by blocking the binding of histamine to its receptors, H1, H2; however others are believed to operate by inhibiting the release of histamine. Examples of antihistamines are chlorpheniramine, diphenhydramine, promethazine, cromolyn sodium, astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofenadine hydrochloride, terphenadine hydrochloride, hydroxyzine hydrochloride, loratidine, meclizine hydrochloride, tripelannamine citrate, tripelennamine hydrochloride, triprolidine hydrochloride.

A "bronchodilator" as used herein, describes agents that antagonizes or reverses bronchoconstriction, a physiological event that occurs typically in early phase asthmatic reactions resulting in decreased lung capacity and shortness of breadth. Example bronchodilators include epinephrine, a broad acting alpha and beta-adrenergic, and the beta-adrenergics albuterol, pirbuterol, metaproterenol, salmeterol, and isoetharine. Bronchodilation can also be achieved through administration of xanthines, including aminophylline and theophylline.

A "glucocorticoid" as used herein describes steroidal based agents having anti-inflammatory acitivity. Glucocorticoid are commonly used to attenuate late phase asthmatic reaction. Example glucocorticoids include, prednisone, beclomethasone dipropionate, triamcinolone acetonide, flunisolide, betamethasone, budesonide, dexamethasone, fludrocortisone acetate, flunisolide, fluticasone propionate, hydrocortisone, methylprednisolone, prednisolone, prednisone and triamcinolone.

A "non-steroidal anti-inflammatory drug" or "NSAID", as used herein describes agents having anti-inflammatory activity that are not steroidal based. Example NSAID's include acetaminophen, aspirin, bromfenac sodium, diclofenac sodium, diflunisal, etodolac, fenoprofen calcium, flurbiprofen, ibuprofen, indomethacin, ketoprofen, meclofenamate sodium, mefenamic acid, nabumetone, naproxen, naproxen sodium, oxyphenbutazone, phenylbutzone, piroxicam, sulindac, tolmetin sodium.

II. Modes for Carrying out the Invention

A. Polypeptide and Antibody Preparation

The following description relates primarily to production of the polyeptides or antibodies described herein by culturing cells transformed or transfected with a vector containing nucleic acid encoding the same and purification of the resulting protein or antibody. It is, of course, contemplated that alternative methods, which are well known in the art, may be employed to prepare such polypeptides or antibodies. For instance, such sequences, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the proteins or antibodies described herein may be chemically synthesized separately and combined using chemical or enzymatic methods.

1. Isolation of DNA Encoding the Proteins Described Herein

DNA encoding the proteins described herein may be obtained from a cDNA library prepared from tissue believed to possess the corresponding mRNA and to express it at a detectable level. Accordingly, such human protein-encoding DNA can be conveniently obtained from a cDNA library prepared from human tissue, such as described in the Examples. The protein-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding the desired gene is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Genbank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors containing the proteins or antibodies described herein for production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding the proteins or antiobodies described herein. *Saccharomyces cerevisiae* is a commonly used lower eukaryotic host microorganism. Others include. *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Biol/Technology*, 9:968-975 (1991)) such as, e.g., *K. lactis* (MW98-8C, CBS683, CBS4574; Louvencourt et al., *J. Bacteriol.*, 154(2): 737-42 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Biol/Technology*, 8:135 (1990)), *K. thermotolerans*, and *K. marxianus; yarrowia* (EP 402,226); *Pichia pastoris* (EP 183,070; Sreekrishna et al., *J. Basic Microbiol*, 28:265-278 [1988]); *Candida*; *Trichoderma reesia* (EP 244, 234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112:284-289 [1983];

Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated form of the polypeptides and antibodies described herein are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the polypeptides and antibodies described herein may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Recombinant production of the polypeptides or antibodies may be accomplished not only directly, but also as a fusion polypeptide with a heterologous polypeptide. The heterologous portion may be a signal sequence or other polypeptide having a specific cleavage site at the N-terminus of the mature protein or polypeptide. In general, the signal sequence may be a component of the vector, or it may be a part of the DNA encoding the polypeptide or antibody that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the DNA sequence encoding the polypeptides or antibodies described herein, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the such DNA sequences to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to such DNA sequences.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells may be controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of nucleic acid encoding the polypeptides or antibodies herein by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptides or antibodies described herein.

Still other methods, vectors, and host cells suitable for adaptation to the synthesis of the polypeptide or antibodies described herein in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot bthtting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against the polypeptides described herein or against a synthetic peptide based on the DNA sequences provided herein or against exogenous sequence fused to DNA encoding such polypeptides and antibodies and encoding a specific antibody epitope.

5. Purification of Polypeptide

Forms of may be recovered from culture medium or from host cell lysates. If membrane-bound, it can be released from the membrane using a suitable detergent solution (e.g. Triton-X 100) or by enzymatic cleavage. Cells employed in expression of the polypeptides or antibodies described herein can be disrupted by various physical or chemical means, such as freeze-thaw cycling, sonication, mechanical disruption, or cell lysing agents.

It may be desired to purify the polypeptides or antibodies described herein from recombinant cell proteins or other polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the polypeptide or antibody. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular polypeptide or antibody produced.

B. Antibody Preparation

In certain embodiments of the invention, the protein of choice is an antibody. Techniques for the production of antibodies, including polyclonal, monoclonal, humanized, bispecific and heteroconjugate antibodies follow.

1) Polyclonal Antibodies.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable used to enhance the immune response.

2) Monoclonal Antibodies.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassus, Va. USA. Human myeloma and mouse-human heteromyeloma cell lines also have been described for the production of human monoclonal antibodies (Kozbor, *J. Immunol.,* 133: 3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The culture medium in which the hybridoma cells are cultured can be assayed for the presence of monoclonal antibodies directed again desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816, 567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3) Humanized Antibodies.

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332:323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et al., Proc. Natl. Acad. Sci. USA, 89:4285 (1992); Presta et al., J. Immmol., 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent(s) in order to generate an immunoconjugate. Alternatively, the humanized antibody may be an intact antibody, such as an intact IgG1 antibody.

4) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); U.S. Pat. No. 5,591,669 and WO 97/17852.

Alternatively, phage display technology can be used to produce human antiobdies and antibody fragments in vitro, from immunoglublin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in seletion of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Curr. Opin Struct. Biol.* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isoalted essentially following the technqieus described by Marks et al., *J. Mol. Biol.* 222:581-597 (1991), or Griffith et al., *EMBO J.* 12:725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human antibodies may also be generated in vitro by activated B cells (see U.S. Pat. Nos. 5,567,610 and 5,229,275).

5) Antibody Fragments

In certain circumstances there are advantages to using antibody fragments, rather than whole antibodies. Smaller fragment sizes allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *J Biochem Biophys. Method.* 24:107-117 (1992); and Brennan et al., *Science* 229:81 (1985)). However, these fragments can now be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ with increase in vivo half-life is described in U.S. Pat. No. 5,869,046. In other embodiments, the antibody of choice is a single chain Fv fragment (scFv). See WO 93/16185; U.S. Pat. No. 5,571,894 and U.S. Pat. No. 5,587,458. The antibody fragment may also be a "linear antibody", e.g., as described in U.S. Pat. No. 5,641,870. Such linear antibody fragments may be monospecific or bispecific.

6) Antibody Dependent Enzyme-Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysozyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as *serratia* protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes" can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The above enzymes can be covalently bound to the polypeptide or antibodies described herein by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

7) Bispecific and Polyspecific Antibodies

Bispecific antibodies (BsAbs) are antibodies that have binding specificities for at least two different epitopes, including those on the same or another protein. Alternatively, one arm can be armed to bind to the target antigen, and another arm can be combined with an arm that binds to a triggering molecule on a leukocyte such as a T-cell receptor molecule (e.g., CD3), or Fc receptors for IgG (FcγR) such as FcγRI (CD64), FcγRII (CD32) and FcγRIII (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., saporin, anti-interferon-α, vinca alkoloid, ricin A chain, methotrexate or radioactive isotope hapten). Examples of known bispecific antibodies include anti-ErbB2/anti-FcgRIII (WO 96/16673), anti-ErbB2/anti-FcgRI (U.S. Pat. No. 5,837,234), anti-ErbB2/anti-CD3 (U.S. Pat. No. 5,821,337).

Methods for making bispecific antibodies are known in the art. Traditional production of full length bispecific antibodies is based on the coexpression of two immunoglobulin heavy chain-light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA,* 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibocis may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (IF).

6) Heteroconjugate Antibodies

Heteroconjugate antibodies are also within the scope of the present invention. Heteroconjugate antibodies are composed of two covalently joined antibodies. For example, one of the antibodies in the heteroconjugate can be coupled to avidin, the other to biotin. Such antibodies have, for example, been proposed to target immune system cells to unwanted cells, U.S. Pat. No. 4,676,980, and for treatment of HIV infection. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

7) Effector Function Engineering

It may be desirable to modify the antibody of the invention with respect to effector function, so as to enhance the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp. Med.* 176: 1191-1195 (1992) and Shopes, *J. Immunol.* 148: 2918-2922 (1992). Homodimeric antibodies with enhanced anti-tumor activity may also be prepared using heterobifunctional crosslinkers as described in Wolff et al., *Cancer Research* 53: 2560-2565 (1993). Alternatively, an antibody can be engineered that has dual Fc regions and may thereby have enhanced complement lysis and ADCC capabilities. See Stevenson et al., *Anti-Cancer Drug Design* 3: 219-230 (1989).

8) Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates include BCNU, streptozoicin, vincristine, vinblastine, adriamycin and 5-fluorouracil.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAM, and PAP-S), *momordica charantia* inhibitor, curcin, crotin, sapaonaria officinalis inhibitor, gelonin, mitogellin, restrictocin, phenomycin, enomycin, and the tricothecenes.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-snsitive linker, dimethyl linker or disulfide-containing linker (Chari et al., *Cancer Res.* 52:127-131 (1992)) may be used.

Additionally, the small molecule toxins such as calicheamicin, maytansine (U.S. Pat. No. 5,208,020), trichothene and CC1065 are also contemplated an conjugatable toxins for use with the inventive formulation. In one embodiment the full length antibody or antigen binding fragments thereof can be conjugated to one or more maytansinoid molecules (e.g., about 1 to about 10 maytansinoid molecules per antibody molecule). Maytansinoids are mitototic inhibitors which act by inhibiting tubulin polymerization. Maytansinoids, isolated from natural sources or prepared synthetically, including maytansine, maytansinal and derivatives and analogues thereof have been described, see e.g., U.S. Pat. No. 5,208,020 and references cited therein (see col. 2, line 53 to col. 3, line 10) and U.S. Pat. Nos. 3,896,111 and 4,151,042. Method of preparing antibody-maytansinoid conjugates are also described in U.S. Pat. No. 5,208,020. In a preferred embodiment, a maytansinoid is linked to the antibody via a disulfide or other sulfur-containing linker group. Maytansine may, for example, be converted to May-SS-Me, which may be reduced to May-SH3 and reacted with modified antibody to generate a maytansinoid-antibody immunoconjugate. Chari et al., *Cancer Res.* 52: 127-131 (1992). The antibody can be modified by known methods and the antibody containing free or protected thiol groups is then reacted with a disulfide containing maytansinoid to produce the conjugate. The cytotoxicity of the antibody-maytansinoid conjugate can be measured in vitro or in vivo by known methods and the $IC_{50}$ determined.

Calicheamicin is another immunoconjugate of interest. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N aceytl $\gamma_1^1$, PSAG and $\theta_1^1$ (Hinman et al., Cancer Res. 53:3336-3342 (1993) and Lode et al., Cancer Res. 58:2925-2928 (1998)). Other anti-tumor drugs that the antibody can be conjugated to include QFA which is an antifolate. Both calicheamicin and QFA have intracellular sites of actions and do not readily corss the plasma membrane. Therefore, cellular uptake of these agents through antibody mediated internalization greatly enhances their cytotoxic effects.

Immunoconjugates formed between an antibody and a compound with nucleolytic activity (e.g., a ribonuclease or DNA endonuclease such as deoxyribonuclease, DNase) are also contemplated.

The antibody may also be conjugated to a highly radioactive atom. A variety of radionuclides are available for the production of radioconjugated antibodies. Examples include $At^{211}$, $Bi^{212}$, $I^{131}$, $In^{131}$, $Y^{90}$, $Re^{186}$, $Re^{188}$, $Sm^{153}$, $P^{32}$ and $Pb^{212}$ and radioactive isotopes of Lu. When the conjugate is used for diagnosis, it may comprise a radioactive atom for scintigraphic studies, for example $Tc^{99}$ or $I^{123}$, or a spin label for nuclear magnetic resonance (nmr) imaging (also known as magnetic resonance imaging, mri), wuch as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place or hydrogen. Labels such $Tc^{99}$ or $I^{123}$, $Re^{186}$, $Re^{188}$ and $In^{111}$ can be attached via a cysteine residue in the peptide. Yttrium-90 can be attached via a lysine residue. The IODOGEN® method can be used to incorporate iodine-123, Fraker et al., *Biohem. Biophys. Res. Commun.* 80:49-57 (1978). Other methods of conjugating radionuclides are described in "Monoclonal Antibodies in Immunoscintigraphy," (Chatal, CRC Press 1989).

Alternatively, a fusion protein comprising the antibody and the cytotoxic agent may be made by recombinant techniques or peptide synthesis. The length of DNA may comprise respective regions encoding the two portions of the conjugate either adjacent to one another or separated by a region encoding a linker peptide which does not destroy the desired properties of the conjugate.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

9) Immunoliposomes

The antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.* 81(19):1484 (1989).

10) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacrylate) microcapsules, respectively), in colloidal drug delivery systems (for example, liposomes, albumin microspheres, microemulsions, nano-particles and nanocapsules), or in macroemulsions. Such techniques and other suitable formulations are disclosed in *Remington: The Science and Practice of Pharmacy,* 20th Ed., Alfonso Gennaro, Ed., Philadelphia College of Pharmacy and Science (2000).

C. Lyophilized Formulations

The formulations described herein may also be prepared as reconstituted lyophilized formulations. The proteins or antibodies described herein are lyophilized and then reconstituted to produce the reduced-viscosity stable liquid formulations of the invention. In this particular embodiment, after preparation of the protein of interest as described above, a "pre-lyophilized formulation" is produced. The amount of protein present in the pre-lyophilized formulation is determined taking into account the desired dose volumes, mode(s) of administration etc. For example, the starting concentration of an intact antibody can be from about 2 mg/ml to about 50 mg/ml, preferably from about 5 mg/ml to about 40 mg/ml and most preferably from about 20-30 mg/ml.

1) Preparation of Lyophilized Formulations

The protein to be formulated is generally present in solution. For example, in the elevated ionic strength reduced viscosity formulations of the invention, the protein may be present in a pH-buffered solution at a pH from about 4-8, and preferably from about 5-7. The buffer concentration can be from about 1 mM to about 20 mM, alternatively from about 3 mM to about 15 mM, depending, for example, on the buffer and the desired tonicity of the formulation (e.g. of the reconstituted formulation). Exemplary buffers and/or salts are those which are pharmaceutically acceptable and may be created from suitable acids, bases and salts thereof, such as those which are defined under "pharmaceutically acceptable" acids, bases or buffers.

In one embodiment, a lyoprotectant is added to the pre-lyophilized formulation. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. However, exemplary lyoprotectant concentrations in the pre-lyophilized formulation are from about 10 mM to about 400 mM, alternatively from about 30 mM to about 300 mM, alternatively from about 50 mM to about 100 mM. Examplery lyoprotectants include sugars and sugar alcohols such as sucrose, mannose, trehalose, glucose, sorbitol, mannitol. However, under particular circumstances, certain lyoprotectants may also contribute to an increase in viscosity of the formulation. As such, care should be taken so as to select particular lyoprotectants which minimize or neutralize this effect. Additional lyoprotectants are described above under the definition of "lyoprotectants", also referred herein as "pharmaceutically-acceptable sugars".

The ratio of protein to lyoprotectant can vary for each particular protein or antibody and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In a preferred embodiment, it may be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); polyoxamers (e.g. poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces particulate formation of the reconstituted protein and minimizes the formation of particulates after reconstitution. For example, the surfactant may be present in the pre-lyophilized formulation in an amount from about 0.001-0.5%, alternatively from about 0.005-0.05%.

A mixture of the lyoprotectant (such as sucrose or trehalose) and a bulking agent (e.g. mannitol or glycine) may be used in the preparation of the pre-lyophilization formulation. The bulking agent may allow for the production of a uniform lyophilized cake without excessive pockets therein etc. Other pharmaceutically acceptable carriers, excipients or stabilizers such as those described in *Remington's Pharmaceutical Sciences* 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, it may be desirable to provide two or more antibodies which bind to the desired target (e.g., receptor or antigen) in a single formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, optional lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). Optionally, a secondary drying stage may also be performed depending upon the desired residual moisture level in the product. The temperature at which the secondary drying is carried out ranges from about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

2. Reconstitution of a Lyophilized Formulation

Prior to administration to the patient, the lyophilized formulation is reconstituted with a pharmaceutically acceptable diluent such that the protein concentration in the reconstituted formulation is at least about 50 mg/ml, for example from about 50 mg/ml to about 400 mg/ml, alternatively from about 80 mg/ml to about 300 mg/ml, alternatively from about 90 mg/ml to about 150 mg/ml. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/ml, or from about 10-40 mg/ml protein in the reconstituted formulation). In certain embodiments, the protein concentration in the reconstituted formulation is significantly higher than that in the pre-lyophilized formulation. For example, the protein concentration in the reconstituted formulation may be about 2-40 times, alternatively 3-10 times, alternatively 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are ≥10 μm in size.

D. Liquid Formulations

Therapeutic formulations are prepared for storage by mixing the active ingredient having the desired degree of purity with optional pharmaceutically acceptable carriers, excipients or stabilizers (*Remington's Pharmaceutical Sciences*

18th edition, Mack Publishing Co., Easton, Pa. 18042 [1990]). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

When the therapeutic agent is an antibody fragment, the smallest inhibitory fragment which specifically binds to the binding domain of the target protein is preferred. For example, based upon the variable region sequences of an antibody, antibody fragments or even peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90: 7889-7893 [1993]).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives are added to retard microbial growth, and are typically present in a range from 0.2%-1.0% (w/v). Suitable preservatives for use with the present invention include (such as octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid a composition. When used with large, charged biomolecules such as proteins and antibodies, they are often termed "stabilizers" because the can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), Pluronic® polyols, Triton®, polyoxyethylene sorbitan monoethers (Tween®-20, Tween®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, macroemulsions, nano-particles and nanocapsules) or in macroemulsions. Such techniques are disclosed in *Remington's Pharmaceutical Sciences* 18th edition, supra.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon- (rhIFN-), interleukin-2, and MN rpg 120. Johnson et al., *Nat. Med.* 2: 795-799 (1996); Yasuda et al., *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds., (Plenum Press: New York, 1995), pp. 439-462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in *Biodegradable Polymers as Drug Delivery Systems* (Marcel Dekker; New York, 1990), M. Chasin and R. Langer (Eds.) pp. 1-41.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Liposomal or proteinoid compositions may also be used to formulate the proteins or antibodies disclosed herein. See U.S. Pat. Nos. 4,925,673 and 5,013,556.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have a solubility in water (at 20° C.) of at least about 20 mg/ml, alternatively at least about 100 mg/ml, alternative at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

E. Methods of Treatment:

For the prevention or treatment of disease, the appropriate dosage of an active agent, will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

A preferred method of treatment is the treatment of IgE-mediated disorders. IgE mediated disorders includes atopic disorders, which are characterized by an inherited propensity to respond immunologically to many common naturally occurring inhaled and ingested antigens and the continual production of IgE antibodies. Specific atopic disorders includes allergic asthma, allergic rhinitis, atopic dermatitis and allergic gastroenteropathy. Atopic patients often have multiple allergies, meaning that they have IgE antibodies to, and symptoms from, many environmental allergens, including pollens, fungi (e.g., molds), animal and insect debris and certain foods.

However disorders associated with elevated IgE levels are not limited to those with an inherited (atopic) etiology. Other disorders associated with elevated IgE levels, that appear to be IgE-mediated and are treatable with the formulations of this present invention include hypersensitivity (e.g., anaphylactic hypersensitivity), eczema, urticaria, allergic bronchopulmonary aspergillosis, parasitic diseases, hyper-IgE syndrome, ataxia-telangiectasia, Wiskott-Aldrich syndrome, thymic alymphoplasia, IgE myeloma and graft-versus-host reaction.

Allergic rhinitis, also known as allergic rhinoconjunctivitis or hay fever, is the most common manifestation of an atopic reaction to inhaled allergens, the severity and duration of which is often correlative with the intensity and length of exposure to the allergen. It is a chronic disease, which may first appear at any age, but the onset is usually during childhood or adolescence. A typical attack consists of profuse watery rhinorrhea, paroxysmal sneezing, nasal obstruction and itching of the nose and palate. Postnasal mucus drainage also causes sore throat, throat clearing and cough. There can also be symptoms of allergic blepharoconjunctivitis, with intense itching of the conjunctivae and eyelids, redness, tearing, and photophobia. Severe attacks are often accompanied by systemic malaise, weakness, fatigue, and sometime, muscle soreness after intense periods of sneezing.

Asthma, also known as reversible obstructive airway disease, is characterized by hyperresponsiveness of the tracheobronchial tree to respiratory irritants and bronchoconstrictor chemicals, producing attacks of wheezing, dyspnea, chest tightness, and cough that are reversible spontaneously or with treatment. It is a chronic disease involving the entire airway, but varies in severity from occasional mild transient episodes to severe, chronic, life-threatening bronchial obstruction. Asthma and atopy may coexist, but only about half of asthmatics are also atopic, and an even smaller percentage of atopic patients also have asthma. However, atopy and asthma are not entirely independent in that asthma occurs more frequently among atopic than amongst nonatopic individuals, especially during childhood. Asthma has further been historically broken down into two subgroups, extrinsic asthma and intrinsic asthma.

Extrinsic asthma, also known as allergic, atopic or immunologic asthma, is descriptive of patients that generally develop asthma early in life, usually during infancy or childhood. Other manifestations of atopy, including eczema or allergic rhinitis often coexist. Asthmatic attacks can occur during pollen seasons, in the presence of animals, or on exposure to house dust, feather pillows, or other allergens. Skin tests show positive wheal-and-flare reactions to the causative allergens. Interestingly, total serum IgE concentrations is frequently elevated, but is sometimes normal.

Intrinsic asthma, also known as nonallergic or idopathic asthma, typically first occurs during adult life, after and apparent respiratory infection. Symptoms include chronic or recurrent bronchial obstruction unrelated to pollen seasons or exposure to other allegens. Skin tests are negative to the usual atopic allergens, serum IgE concentration is normal. Additional symptoms include sputum blood and eosinophilia. Other schemes for classifying asthma into subgroups, like aspirin-sensitive, exercise-induced, infectious and psychologic merely define external triggering factors that affect certain patients more so than others.

Finally, it is important to note that while some classifications have historically associated only allergic asthma with IgE dependency, there is now strong statistically significant data showing a correlation between IgE and asthma (both allergic and non-allergic). Chapter 27, "The Atopic Diseases", A. I. Terr in Medical Immunology, 9th Ed., Simon and Schuster, Stites et al, Ed. (1997). As a result, the term "IgE-mediated disorders", for purposes of this patent application, includes both allergic and non-allergic asthma.

Physical signs of an asthma attack include tachypnea, audible wheezing, and use of the accessory muscles of respiration. Rapid pulse and elevated blood pressure are also typically present, as are elevated levels of eosinophils in the peripheral blood and nasal secretions. Pulmonary functions show a decrease in flow rates and 1 second forced expiratory volume ($FEV_1$). The total lung capacity and functional residual capacity are typically normal or slightly increased, but may be decreased with extreme bronchospasm.

The pathology of asthma can be distinguished by early phase and late phase reactions. The early phase is characterized by smooth muscle contraction, edema and hypersecretion, while the late phase reactions by cellular inflammation. Asthma can be induced by various non-specific triggers including infections (e.g., viral respiratory infections), physiologic factors (e.g., exercise, hyperventilation, deep breathing, psychologic factors), atmospheric factors (e.g., sulfur dioxide, ammonia, cold air, ozone, distilled water vapor), ingestants (e.g., propranolol, aspirin, nonsteroidal anti-inflammatory drugs), experimental inhalants (e.g., hypertonic solutions, citric acid, histamine, methacholine, prostaglandin $F_{2\alpha}$) and occupational inhalants (e.g., isocyantes). Various additional occupational or environmental allergens that cause allergic asthma can include, animal products, insect dusts, sea creatures, plant products, fruits, seeds, leaves and pollens, organic dyes and inks, microbial agents, enzymes, therapeutic agents, sterilizing agents, inorganic and organic chemicals.

Atopic dermatitis, also known as eczema, neurodermatitis, atopic eczema or Besnier's prurigo, is common chronic skin disorder specific to a subset of patients with the familial and immunologic features of atopy. The essential feature is a pruritic dermal inflammatory response, which induces a characteristic symmetrically distributed skin eruption with predilection for certain sites. There is also frequent overproduction of IgE by B lymphocytes. While atopic dermatitis is classified as a cutaneous form of atopy because it is associated with allergic rhinitis and asthma and high IgE levels, the severity of the dermatitis, however, does not always correlate with exposure to allergens on skin testing, and desensitization (unlike other allergic diseases) is not effective treatment. While high serum IgE is confirmatory of a diagnosis of allergic asthma, normal levels do not preclude it. Onset of the disease can occur at any age, and lesions begin acutely with erythematous edematous papule or plaque with scaling. Itching leads to weeping and crusting, then to chronic lichenification. On the cellular level, acute lesion is edemous and the dermis is infiltrated with mononuclear cells, CD4 lymphocytes. Neutrophils, eosinophils, plasma cells and basophils are rare, but degranulated mast cells are present. Chronic lesions feature epidermal hyperplasia, hyperkeratosis and parakeratosis, and the dermis is infiltrated with mononuclear cells, Langerhans' cells and mast cells. There may also be focal areas of fibrosis, including involvement of the perineurium of small nerves.

Allergic gastroenteropathy, also known as eosinophilic gastroenteropathy, is an unusual atopic manifestation in which multiple IgE food sensitivities are associated with a local gastrointestinal tract mucosal reaction. It is rare in adults, but more common, but transient, in infants. The condition results when ingested food allergens react with local IgE antibodies in the jejunal mucosa liberate mast cell mediators, resulting in gastrointestinal symptoms shortly after the meal. Continued exposure produced chronic inflammation, resulting in gastrointestinal proteins loss and hypoproteinemic edema. Blood loss through the inflamed intestinal mucosa may be significant enough to cause iron deficiency anemia. The allergic reaction occurs locally in the upper gastrointestinal mucosa following allergen exposure, but resolves with allergen avoidance.

Anaphylaxis and urticaria are clearly IgE-mediated, but they lack genetic determinants, and have no predilection for atopic individuals. Anaphylaxis is an acute, generalized allergic reaction with simultaneous involvement of several organ systems, usually cardiovascular, respiratory, cutaneous and gastrointestinal. The reaction is immunologically mediated, and it occurs on exposure to an allergen to which the subject has been previously sensitized. Urticaria and angioedema refers to the physical swelling, erythema and itching resulting from histamine stimulated receptor in superficial cutaneous blood vessels, and is the hallmark cutaneous feature of systemic anaphylaxis. Systemic anaphylaxis is the occurrence of an IgE-mediated reaction simultaneously in multiple organs resulting from drug, insect venom or food. It is caused suddenly by allergen induced, mast cell loaded IgE, resulting in profound and life-threatening alteration in the functioning of various vital organs. Vascular collapse, acute airway obstruction, cutaneous vasodilation and edema, and gastrointestinal and genitourinary muscle spasm occur almost simultaneously, although not always to the same degree.

The pathology of anaphylaxis includes angioedema and hyperinflated lungs, with mucous plugging of airways and focal atelectasis. On a cellular level, the lungs appear similarly as during an acute asthma attack, with hypersecretion of bronchial submucosal glands, mucosal and submucosal edema, peribronchial vascular congestion and eosinophilia in the bronchial walls. Pulmonary edema and hemorrhage may be present. Bronchial muscle spasm, hyperinflation, and even rupture of alveoli may also be present. Important feature of human anaphylaxis include edema, vascular congestion, and eosinophilia in the lamina propria of the larynx, trachea, epiglottis and hypopharynx. Exposure to the allergen may be through ingestion, injection, inhalation or contct with skin or mucous membrane. The reaction begins within seconds or minutes after exposure to the allergen. There may be an initial fright or sense of impending doom, followed rapidly by symptoms in one or more target organ systems: cardiovascular, respiratory, cutaneous and gastrointestinal.

The allergens responsible for anaphylaxis differ from those commonly associated with atopy. Foods, drugs, insect venoms or latex are the common sources. Food allergens includes those fond in crustaceans, mollusks (e.g., lobster, shrimp, crab), fish, legumes (e.g., peanuts, peas, beans, licorice), seeds (e.g. sesame, cottonseed, caraway, mustar, flaxseed, sunflower), nuts, berries, egg whites, buckwheat and milk. Drug allergens include those found in heterologous proteins and polypeptides, polysaccharides and haptenic drugs. Insect allergens include Hymenoptera insects, including the honeybee, yellow jacket, hornet, wasp and fire ant.

While epinephrine is the typical treatment for anaphylaxis, antihistamine or other histamine blockers are typically prescribed for less severe urticaria or angioedemic reaction.

F. Combination Therapies

The method of the invention can be combined with known methods of treatment for IgE-mediated disorder, either as combined or additional treatments steps or as additional components of a therapeutic formulation.

For example, antihistamines, especially non-sedating antihistamines may be administered before, prior to, or commensurate with the anti-IgE antibodies of the invention. Suitable antihistamines include those of the alkylamine (e.g., chlorpheniramine), ethanolamine (e.g., diphenhydramine) and phenothiazine (e.g., promethazine). While many antihistamines antagonize the pharmacological effects of histamine by blocking its receptor sites on the effector cells; other common antihistamine drugs operate by blocking histamine release from mast cells that have been sensitized and armed with allergen-specific IgE (e.g., cromolyn sodium). Example antihistamines include astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofendadine hydrochloride, terphenadine hydrochloride, hydroxyzine hydrochloride, loratidine, meclizine hydrochloride, tripelannamine citrate, tripelennamine hydrochloride, triprolidine hydrochloride.

Particular symptoms of IgE-mediated disorders (e.g., early phase reactions) can be ameliorated with sympathomimetics or drugs having bronchodialator effect. Epinephrine is a broad acting alpha and beta-adrenergic often administered subcutaneously in a does of 0.2-0.5 mL of 1:100 aqueous solution. A longer acting form of epinephrine (i.e., terbutaline) in 1:200 suspension is also used when a longer duration effect is desired. Suitable additional beta-adrenergics include albuterol, pirbuterol, metaproterenol, salmeterol, isoetharine and formoterol for administration nasally (e.g., hand-held nebulizer, intermittent positive-pressure breathing device, or metered-dose pressurized inhalers) or orally.

Bronchodilation can also be achieved through administration of xanthines, especially when they are administered in combination with the above sympathomimetic drugs. Example xanthines include aminophylline (iv. 250-500 mg) and theophylline (oral, 10-20 µg/ml serum concentration).

Other symptoms from various IgE-mediated disorders (e.g., late phase reactions) can be attenuated by treatment with glucocorticoids or other drugs having anti-inflammatory effects. Prednisone (30-60 mg daily) is administered systemically for severe attacks, while beclomethasone dipropionate, triamcinolone acetonide and flunisolide are administered in aerosolized form as long-term maintenance therapy. Additionaly coricosteroids that have anti-inflammatory effects include: betamethasone, budesonide, dexamethasone, fludrocortisone acetate, flunisolide, fluticasone propionate, hydrocortisone, methylprednisolone, prednisolone, prednisone, triamcinolone.

Non-steroidal anti-inflammatory drugs that may also be used in combination with the therapeutic methods of the invention include, acetaminophen, aspirin, bromfenac sodium, diclofenac sodium, diflunisal, etodolac, fenoprofen calcium, flurbiprofen, ibuprofen, indomethacin, ketoprofen, meclofenamate sodium, mefenamic acid, nabumetone, naproxen, naproxen sodium, oxyphenbutazone, phenylbutzone, piroxicam, sulindac, tolmetin sodium.

Additionally, the maximum therapeutic benefit may also be achieved with the administration of decongestants (e.g., phenylephrine, phenylpropanolamine, pseudoephadrin), cough suppressants (e.g., dextromethorphan, codeine, or hydrocodone) or analgesic (e.g., acetaminophen, aspirin).

Allergen desensitization is a treatment form in which allergens are injected into the patient for the purpose or reducing or eliminating the allergic response. It is also known as allergen immunotherapy, hyposensitization or allergy injection therapy. It is often used in combination with other allergy treatments, but not often as a primary treatment. It has been successful employed when allergen avoidance is impossible. A typical allergen desensitization treatment incorporates subcutaneous injection of sterile allergen in increasing doses once or twice a week until a dose is achieved that produces a transient small local area of inflammation at the injection site. The does is then given on a maintenance schedule once every 2-4 weeks. Allergic desensitization is most often used in the treatment of allergic asthma and allergic rhinitis, althought is has had success in treating anaphylaxis. Desensitization has also been effectively used through the use of adjuvants, such as incomplete Freund's adjuvant, which is an emulsion of aqueous antigen in mineral oil. The physiological effect creates an insoluble liquid depot from which droplets of allergen are gradually released. Another form of allergen desensitization is to polymerize monomeric allergens with glutaraldehyde to create a molecule with relatively low allergenity (i.e., causes allergic response), while retaining an effective degree of immunogenicity.

G. Pharmaceutical Dosages:

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the polypeptides or antibodies described herein are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

H. Administration of the Formulation

The formulations of the present invention, including but not limited to reconstituted formulations, are administered to a mammal in need of treatment with the protein, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

In preferred embodiments, the formulations are administered to the mammal by subcutaneous (i.e. beneath the skin) administration. For such purposes, the formulation may be injected using a syringe. However, other devices for administration of the formulation are available such as injection devices (e.g. the Inject-Ease™ and Genject™ devices); injector pens (such as the GenPen™); auto-injector devices, needleless devices (e.g. MediJector™ and BioJector™); and subcutaneous patch delivery systems.

In a specific embodiment, the present invention is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

Where the protein of choice is an antibody, from about 0.1-20 mg/kg is an initial candidate dosage for administration to the patient, whether, for example, by one or more separate administrations. However, other dosage regimens may be useful. The progress of this therapy is easily monitored by conventional techniques.

Uses for an anti-IgE formulation (e.g., rhuMAbE-25, rhMAbE-26, Hu-901) include the treatment or prophylaxis of IgE-mediated allergic diseases, parasitic infections, interstitial cystitis and asthma, for example. Depending on the disease or disorder to be treated, a therapeutically effective amount (e.g. from about 1-15 mg/kg) of the anti-IgE antibody is administered to the patient.

I. Articles of Manufacture

In another embodiment of the invention, an article of manufacture is provided which contains the formulation and preferably provides instructions for its use. The article of manufacture comprises a container. Suitable containers include, for example, bottles, vials (e.g. dual chamber vials), syringes (such as single or dual chamber syringes) and test tubes. The container may be formed from a variety of materials such as glass or plastic. The container holds the formulation and the label on, or associated with, the container may indicate directions for reconstitution and/or use. The label may further indicate that the formulation is useful or intended for subcutaneous administration. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All citations throughout the disclosure are hereby expressly incorporated by reference.

In another embodiment, the invention provides for an article of manufacture comprising the formulations described herein for administration in an auto-injector device. An auto-injector can be described as an injection device that upon activation, will deliver its contents without additional necessary action from the patient or administrator. They are particularly suited for self-medication of therapeutic formulations when delivery rate must be constant and the time of delivery is greater than a few moments.

EXAMPLE 1

Preparation of Anti-IgE rhuMAbE25 ("E25") Formulation

Formulations of the monoclonal anti-IgE antibody rhuMAbE25 were prepared from E25 bulk residual Lot K9094A (40 mg/ml rhuMAb E25, 85 mM trehalose, 5 mM histidine, pH 6, 0.01% Tween 20) or rhuMAbE25 Q-Pool (5 mg/ml rhuMAb E25, 25 mM Tris, 200 mM NaCl).

Aqueous solutions of rhuMAbE25 was prepared by dialysis into different buffers (20 mM His-HCl and 200 mM Arg-HCl, pH 6.0) at 2-8° C. using a Slide-A-Lyzer Dialysis Cassette (Pierce). The samples were then transferred into the sample reservoir of a Centricon-30 centrifugal microconcentrators (Amicon). The proteins were concentrated by spinning the Centricon-3 concentrator at 4000-5000 g until the desired protein concentration is achieved.

The samples were then concentrated to ~150 mg/ml of rhuMAb E25 using ultrafiltration. Tween 20 was added to each preparation to a final concentration of 0.02%. All formulations were filtered, aseptically filled into 3 cc FormaVitrum vials and stoppered with 13-mM Diakyo stoppers in a Class 100 room.

EXAMPLE 2

Method and Materials

Stability Studies:

All formulations were filled at 1 ml in 3 cc FormaVitrum glass vials and stoppered with 13-mm Diakyo stoppers in a Class 100 sterile filling suite. Vials were placed at −70, 2-8, 15, 30 and 40° C. in light impermeable containers.

Agitation Study:

Aliquots of each formulation were placed in the glass vials. Vials were agitated horizontally on a Glas-Col Bench Top Shaker at room temperature. The shaker was set at 70 with an arm length of 30 cm (maximum). After agitation, samples were inspected and analyzed according to the following protocol.

Freeze-Thawing Study:

Samples of E25 underwent three cycles of freeze-thaw. Each cycle consisted of freezing at −70° C. overnight and subsequently thawing at room temperature for about one hour. After each cycle, samples were inspected visually using a light box to assess the color and clarity of the liquid. Turbidity and soluble aggregates were measured following the protocol described below.

Analytical Methods:

Stability samples were analyzed by the methods outlined in Table 1

Summary of Liquid Formulations

| Formulations | Protein Ranges | Buffer/Ranges | Excipients/Ranges |
|---|---|---|---|
| 80 mg/ml E25 50 mM Histidine-HCl 150 mM Trehalose 0.05% Polysorbate 20 pH 6.0 | 40-150 mg/ml | His-HCl or His-Acetate Ranges: 10 mM-100 mM | Trehalose or Sucrose Sugar Ranges: 20 mM-350 mM Polysorbate: 0.01%-0.1% |
| 150 mg/ml E25 20 mM Histidine-HCl 200 mM ArgHCl 0.02% Polsorbate 20 pH 6.0 | 40-260 mg/ml | His-HCl or His-Acetate Ranges: 10 mM-100 mM | ArgHCl Ranges: 50 mM-200 mM Polysorbate: 0.01%-0.1% |

Stability Data for 150 mg/ml E25 in Histidine and ArgHCl Formulation

| Temp (° C.) | Time (months) | Visual | pH | SEC$^a$ % Monomer | HIC$^b$ % of Main | Potency$^c$ | Turbidity$^d$ |
|---|---|---|---|---|---|---|---|
| 5 | 0 | pass | 6.2 | 99.0 | 64 | 106 | 0.25 |
|   | 1 | pass | 6.0 | 99.2 | 63 | 100 | 0.27 |
|   | 3 | pass | 6.0 | 99.3 | 63 | 111 | 0.25 |
|   | 16 | pass | 6.0 | 98.9 | 62 | 83 | 0.27 |
| 30 | 1 | pass | 5.9 | 98.43 | 54 | 91 | 0.25 |
|   | 3 | Pass | 6.1 | 97.53 | 42 | 65 | 0.30 |
|   | 16 | Pass | 6.0 | 90.63 | 19 | 28 | 0.54 |

TABLE 1

| Analytical Methods | |
|---|---|
| Assay | Purpose |
| Color, Clarity, Appearance$^a$ | Visual inspection of liquid formulations |
| Size Exclusion Chromatography (SEC)$^b$ | Measures % monomer, soluble aggregates and low molecular weight components |
| Hydrophobic Interaction Chromatography (HIC)$^c$ | Measures level of Asp-32 isomerization and free thiol |
| UV Spec Scan (Gravimetric)$^f$ | Measures protein concentration |
| Turbidity (Mean OD 340-360 nm)$^d$ | Measures soluble and insoluble aggregates |
| Activity$^e$ | Determines binding activity of anti-IgE |

$^a$Pass for Color, Appearance and Clarity:

The color, appearance and clarity of the sample were visually assessed against the white and black background of the inspection and compared to an equal volume of negative control. Samples should be carefully swirled to ensure homogenous mixing, but not so vigorously so as to create air bubbles.

$^b$Size Exclusion Chromatography:

A TSK SUPER SW3000 (4.6 × 300 mm) column was used in an HP 1100 chromatography system. The column was loaded with 20 μg protein and eluted in 0.1M potassium phosphate, pH 6.8. The sample was measured at 280 nm by a UV detector.

$^c$Hydrophobic Interaction Chromatography (HIC):

The HIC experiments were conducted using a TSK Phenyl-5PW (7.5 × 75 mm) column (TosoHaas) on an HP 1100 liquid chromatography system. The column was loaded with 28 μg of papain digested Fab fragments and eluted with a concentration gradient of ammonium sulfate in 20 mM Tris buffer from 2M to 0M. The peaks were monitored at 210 nm by a UV detector.

$^d$Turbidity:

The turbidity of samples were determined in a 1-cm path length cuvette using a HP spectrometer. The turbidity was calculated as the average absorbance from 340-360 nm.

$^e$The activity of the anti-IgE monoclonal antibody was determined by a receptor binding inhibition assay. Samples were diluted to fall within the range of the standard curve from 100 and 1.56 μg/ml in an assay diluent containing phosphate buffer, 0.5% BSA, 0.05% polysorbate 20, 0.01% Thimerosol. A microtiter plate was coated with IgE receptor, then incubated with the IgE-biotin and diluted anti-IgE sample. The amount of IgE-Biotin bound to the receptor that correlated with activity of anti-IgE monoclonal antibody was measured using Streptavidin-HRP. The data were analyzed using a 4-parameter logistic curve-fitting program.

$^f$The concentration of antibody was obtained on a Hewlett Packard 8453 diode array spectrophotometer with a 1-cm quartz cuvetter. The concentration was calculated using an absorptivity of 1.5 cm$^{-1}$ (mg/ml).$^{-1}$ Stability Data for 80 mg/ml E25 in Histidine and Trehalose Formulation

| Temp (° C.) | Time (Months) | Visual | pH | SEC [a] % Monomer | HIC [b] % Main | Potency [c] | Turbidity [d] |
|---|---|---|---|---|---|---|---|
| 5 | 0 | Pass | 5.7 | 99.1 | 64 | 100 | 0.20 |
|   | 1 | Pass | 5.8 | 98.7 | 63 | 92 | 0.20 |
|   | 3 | Pass | 5.7 | 98.8 | 63 | 124 | 0.20 |
|   | 6 | Pass | 5.7 | 99.1 | 63 | 97 | 0.21 |
|   | 14 | Pass | 5.7 | 99.0 | 62 | 83 | 0.21 |
|   | 24 | Pass | 5.7 | 98.8 | 62 | 84 | 0.20 |
| 30 | 1 | Pass | 5.8 | 98.7 | 55 | 77 | 0.20 |
|   | 3 | Pass | 5.7 | 97.4 | 41 | 76 | 0.29 |
|   | 6 | Pass | 5.8 | 95.5 | 31 | 48 | 0.38 |
|   | 14 | Pass | 5.7 | 93.1 | 22 | 30 | 0.48 |

[a] Size exclusion chromatography for measuring soluble aggregates and fragments
[b] Hydrophobic interaction chromatography for papain digested E25.
[c] IgE receptor binding inhibition assay
[d] Mean OD (340-360 nm)

Agitation Study:

| | T0 | | | Shaking after 3 days | | |
|---|---|---|---|---|---|---|
| Formulation | Visual | SEC (% Monomer) | Turbidity | Visual | SEC (% Monomer) | Turbidity |
| 1 | Pass | 99.5 | 0.18 | pass | 99.3 | 0.18 |
| 2 | Pass | 99.0 | 0.19 | pass | 99.4 | 0.19 |

Formulation 1: 156 mg/ml E25, 200 mM ArgCl, 23 mM His, 0.02% T20
Formulation 2: 150 mg/ml E25, 182 mM ArgCl, 20 mM His, 0.02% T20

Freeze Thawing Study:

| | T0 | | | After 1st Cycle | | | After 3rd Cycle | | |
|---|---|---|---|---|---|---|---|---|---|
| Formulation | Visual | SEC % Monomer | Turbidity | Visual | SEC % Monomer | Turbidity | Visual | SEC % Monomer | Turbidity |
| 1 | pass | 99.5 | 0.18 | pass | 99.3 | 0.17 | pass | 99.4 | 0.17 |
| 2 | pass | 99.0 | 0.19 | pass | 99.2 | 0.19 | pass | 99.2 | 0.18 |

Formulation 1: 156 mg/ml E25, 200 mM ArgCl, 23 mM His, 0.02% T20
Formulation 2: 150 mg/ml E25, 182 mM ArgCl, 20 mM His, 0.02% T20

EXAMPLE 3

Samples of the anti-IgE monoclonal antibody (E26) liquid formulations were prepared in 20 mM buffers and then stored at 30° C. and 40° C. The stability of E26 was determined by chromatography and activity measurements. The size exclusion chromatography was used for determining the soluble aggregates, and the hydrophobic interaction chromatography of pepsin digested sample was used for measuring isomerization. The activity of sample was monitored by using an IgE receptor binding inhibition assay. As shown in FIGS. 1, 2 and 3, the degradation of E26 is highly dependent on pH of buffers. The E26 appears to be most stable around pH 6.0.

EXAMPLE 4

The particulate formulation is a major challenge for making the high concentration liquid formulation, since it usually increases with increasing of protein concentration under the stressed conditions. FIG. 4 shows the result of agitation study for a concentrated E26 liquid formulation. The formulation was prepared in 20 mM succinate, 192 mM trehalose at pH 6.0 with different concentration of polysorbate 20. The particulate formulation was monitored by turbidity measurement. The result shows that the turbidity of E26 solution increases with agitation time. The addition of at least 0.01% of polysorbate is essential for reducing the particulate formation under the stressed condition. Similar results were also observed for concentrated E25 liquid formulation.

EXAMPLE 5

FIG. 5 shows the liquid formulation of 150 mg/ml E25 prepared by reconstitution of the lyophilized E25. Increasing of salt concentration inhibits the reversible particulate formation and results in the reduction of turbidity reading. Among all the salts tested, the formulation with Arg-HCl appears to have the least turbidity. The effect of salt concentration on lowering the turbidity reading has also been observed for E25 prepared using a TFF process.

EXAMPLE 6

The liquid formulation of E25 in the presence of ArgHCl also appears to have better stability than other liquid formulations. FIGS. 6 and 7 show the stability study of E25 at 150 mg/ml in liquid formulation containing ArgHCl, $CaCl_2$ and $MgCl_2$. For liquid formulations containing ArgHCl with or without sucrose, there is little difference in their stability in terms of turbidity, isomerization and fragmentation. The liquid formulations containing ArgHCl are more stable than the formulation containing $MgCl_2$ and $CaCl_2$.

EXAMPLE 7

FIG. 8 shows the results of a stability study of E25 liquid formulation with acetate and histidine formulations. The formulation with histidine has higher pH than the acetate formulation. The results clearly showed that the E25 in a histidine, ArgHCl liquid formulation are more stable than under other conditions.

EXAMPLE 8

The high concentration of E25 can form a solid gel in the presence of certain ions, such as citrate, succinate and sulfate (table I), particularly at storage temperature of 2-8° C. Using arginine-HCl as an excipient allows us to formulate E25 up to more than 200 mg/ml without gel or precipitate formation.

TABLE 1

Effect of various excipients on gelation of E25 at 125 mg/ml, pH ~6.0

| Excipient | Excipient Concentration MM | Preparation | Turbidity at T0 (340-360 nm) | Antibody Concentration mg/ml | Visual Appearance |
|---|---|---|---|---|---|
| SWFI | | Lyo Recon | 0.21 | 125 | Clear |
| NaCl | 188 | Lyo Recon | 0.25 | 125 | Clear |
| Succinate | 94 | Lyo Recon | 0.31 | 125 | Gel |

TABLE 1-continued

Effect of various excipients on gelation of E25 at 125 mg/ml, pH ~6.0

| Excipient | Excipient Concentration MM | Preparation | Turbidity at T0 (340-360 nm) | Antibody Concentration mg/ml | Visual Appearance |
|---|---|---|---|---|---|
| Succinate | 19 | Lyo Recon | 0.28 | 125 | Gel |
| Citcrate | 188 | Lyo Recon | Pending | 125 | Gel |
| Citrate | 19 | Lyo Recon | Pending | 125 | Gel |
| $Na_2SO_4$ | Pending | Lyo Recon | Pending | 125 | Gel |
| $Na_2SO_4$ | Pending | Lyo Recon | Pending | 125 | Opalescent |
| Phosphate | Pending | Lyo Recon | Pending | 125 | Opalescent |
| Acetate | 188 | Lyo Recon | Pending | 125 | Clear |
| Acetate | 94 | Lyo Recon | Pending | 125 | Clear |
| Acetate | 19 | Lyo Recon | Pending | 125 | Clear |
| Histidine | 94 | Lyo Recon | 0.19 | 125 | Clear |
| Histidine | 47 | Lyo Recon | 0.24 | 125 | Clear |
| Arginine-HCl | 150 | Lyo Recon | 0.25 | 137 | Clear |
| Arginine-HCl | 200 | TFF | 0.19 | 162 | Clear |
| Arginine-$SO_4$ | 150 | Lyo Recon | 0.27 | 137 | Gel |
| $CaCl_2$ | 125 | TFF | 0.32 | 147 | Clear |
| $MgCl_2$ | 125 | TFF | 0.48 | 147 | Opalescent |

EXAMPLE 9

Expression of Protein or Antibody in E. coli

This example illustrates preparation of an unglycosylated form of a desired protein or antibody by recombinant expression in E. coli.

The DNA sequence encoding the desired protein or antibody is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the coding region of the desired protein or antibody, lambda transcriptional terminator, and an argU gene. Additionally, the vector may include at least not insignificant portions of the untranslated 5' and 3' sections of the native sequence nucleic acid encoding the desired protein or antibody.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized desired protein or antibody can then be purified using a metal chelating column under conditions that allow tight binding of the solubilized protein or antibody.

The desired protein or antiobdy may be expressed in E. coli in a poly-His tagged form, using the following procedure. The DNA encoding the desired protein or antibody is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) Ion galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 mM. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed, phase resin. Aggregated species are usually eluted at higher acetonitrile concentrations. In addition to resolving misfolded forms of proteins from the desired form, the reversed phase step also removes endotoxin from the samples.

Fractions containing the folded desired protein or antibody are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

EXAMPLE 10

Expression of Protein or Antibody in Mammalian Cells

This example illustrates preparation of a potentially glycosylated forms of the desired protein or antibody by recombinant expression in mammalian cells.

The vector, pRK5 (see EP 307,247, published Mar. 15, 1989), is employed as the expression vector. Optionally, DNA encoding the desired protein or antibody is ligated into pRK5 with selected restriction enzymes to allow insertion such DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg if DNA encoding the desired protein or antibody ligated into pRK5 is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 pEi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the desired protein or antibody. The cultures containing transfected cells may undergo further incubation (in serum free medium) and the medium is tested in selected bioassays.

In an alternative technique, the desired protein or antibody may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg DNA encoding the desired protein or antibody ligated into pRK5 is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing the expressed desired protein or antibody can then be concentrated and purified by any selected method, such as dialysis and/or column chromatography.

In another embodiment, the desired protein or antibody can be expressed in CHO cells. The DNA encoding the desired protein or antibody ligated into pRK5 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the desired protein or antibody, the culture medium may be replaced with serum free medium. Preferably, the cultures are incubated for about 6 days, and then the conditioned medium is harvested. The medium containing the expressed desired protein or antiobody can then be concentrated and purified by any selected method.

Epitope-tagged variants of the desired protein or antibody may also be expressed in host CHO cells. The DNA encoding the desired protein or antibody ligated into pRK5 may be subcloned out of the pRK5 vector. The subclone insert can undergo PCR to fuse in frame with a selected epitope tag such as a poly-his tag into a Baculovirus expression vector. The poly-his tagged DNA encoding the desired protein or antibody insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged desired protein or antibody can then be concentrated and purified by any selected method, such as by $Ni^{2+}$-chelate affinity chromatography.

The desired protein or antibody may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains), of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology,* Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number and pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated at 4° C., in 20 mM Hepes, pH 7.4, buffer containing 0.3 M NaCl and 5 mM imidazole at a flow rate of 4-5 ml/min. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL, of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

EXAMPLE 11

Expression of Protein or Antibodies in Yeast

The following method describes recombinant expression of the desired protein or antibody in yeast.

First, yeast expression vectors are constructed for intracellular production or secretion of the desired protein or antibody from the ADH2/GAPDH promoter. DNA encoding desired protein or antibody and the promoter is inserted into suitable restriction enzyme sites in the selected plasmid in order to direct intracellular expression. For secretion, DNA encoding the desired protein or antibody can be cloned into the selected plasmid, together with DNA encoding the ADH2/GAPDH promoter, a native signal peptide or other mammalian signal peptide, or, for example, a yeast alpha-factor or invertase secretory siglnal/leader sequence, and linker sequences (if needed) for expression of the desired protein or antibody.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

The recombinant protein or antibody can subsequently be isolated and purified by removing the yeast cells from the fermentation medium by centrifugation and then concentrating the medium using selected cartridge filters. The concentrate containing the recombinant protein or antibody may further be purified using selected column chromatography resins.

EXAMPLE 12

Expression of the Protein or Antibody in Baculovirus-Infected Insect Cells

The following method describes recombinant expression of the desired protein or antibody in Baculovirus-infected insect cells.

The sequence coding for the desired protein or antibody is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding the desired portion of the protein or antibody, such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by OReilley et al., *Baculovirus expression vectors: A Laboratory Manual*, Oxford: Oxford University Press (1994).

Expressed poly-his tagged protein or antibody can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged protein or antibody are pooled and dialyzed against loading buffer.

Alternatively, purification of the IgG tagged (or Fc tagged) protein or antibody can be performed using known chromatography techniques, including for instance, Protein A or protein G column chromatography.

EXAMPLE 13

Preparation of Antibodies

This example illustrates preparation of monoclonal antibodies which can specifically bind the protein of interest or the desired antigen.

Techniques for producing the monoclonal antibodies are known in the art and are described, for instance, in Goding, supra. Immunogens that may be employed include purified desired protein or target antibody, fusion proteins containing the desired protein or target antigen, and cells expressing such recombinant protein or antigen on the cell surface. Selection of the immunogen can be made by the skilled artisan without undue experimentation.

Mice, such as Balb/c, are immunized with the desired protein or target antigen immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect antibodies direct to the desired protein or antigen.

After a suitable antibody titer has been detected, the animals "positive" for antibodies can be injected with a final intravenous injection of the desired protein or target antigen. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the desired protein or target antigen. Determination of "positive" hybridoma cells secreting the such monoclonal antibodies is within the skill in the art.

The positive hybridoma cells can be injected intraperitoneally into syngeneic Balb/c mice to produce ascites containing such monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

EXAMPLE 14

Purification of the Desired Protein Using Specific Antibodies

The desired protein, in either native or recombinant form, may be purified by a variety of standard techniques in the art of protein purification. For example, pro-polypeptide, mature polypeptide, or pre-polypeptide forms of the desired protein may be purified by immunoaffinity chromatography using antibodies specific fora the desired protein. In general, an immunoaffinity column is constructed by covalently coupling the antibody that specifically binds the desired protein to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of the desired protein by preparing a fraction from cells expressing it in a soluble form. This preparation is derived by solubilization of the whole cell or of a subcellular fraction obtained via differential centrifugation by the addition of detergent or by other methods well known in the art. Alternatively, soluble protein containing a signal sequence may be secreted in useful quantity into the medium in which the cells are grown.

The solublized preparation containing the desired protein is passed over the immunoaffinity column, and the column is washed under conditions that allow the preferential absorbance of the desired protein (e.g., high ionic strength buffers in the presence of detergent). Then, the column is eluted under conditions that disrupt antibody to protein binding (e.g., a low pH buffer such as approximately pH 2-3, or a high concentration of a chaotrope such as urea or thiocyanate ion), and the desire protein is then collected.

What is claimed is:

1. A stable, liquid formulation of low turbidity comprising (a) an anti-IgE antibody in an amount of about 150 mg/ml, (b) arginine-HCl in an amount of 200 mM, (c) histidine in an amount of 20 mM, and (d) polysorbate in an amount of 0.01 to 0.1%, and where the formulation further has a pH of 6.0; wherein the anti-IgE antibody comprises a light chain comprising the amino acid sequence of SEQ ID NO:1 and a heavy chain comprising the amino acid sequence of SEQ ID NO:4.

2. An article of manufacture comprising a container enclosing a stable, liquid formulation of low turbidity comprising (a) an anti-IgE antibody in an amount of about 150 mg/ml, (b) arginine-HCl in an amount of 200 mM, (c) histidine in an amount of 20 mM, and (d) polysorbate in an amount of 0.01 to 0.1%, and where the formulation further has a pH of 6.0; wherein the anti-IgE antibody comprises a light chain comprising the amino acid sequence of SEQ ID NO:1 and a heavy chain comprising the amino acid sequence of SEQ ID NO:4.

3. The article of manufacture of claim 2, wherein the container is a syringe.

4. The article of manufacture of claim 3, wherein the syringe is further contained within an injection device.

5. The article of manufacture of claim 4, wherein the injection device is an auto-injector.

6. A stable, liquid formulation of low turbidity comprising (a) an anti-IgE antibody in an amount of about 150 mg/ml, (b) arginine-HCl in an amount of 200 mM, (c) histidine in an amount of 20 mM, and (d) polysorbate in an amount of 0.01 to 0.1%, and where the formulation further has a pH of 6.0;
wherein the anti-IgE antibody is produced by a method comprising
(1) culturing cells transformed or transfected with a vector containing nucleic acid encoding an antibody comprising a light chain comprising the amino acid sequence of SEQ ID NO:1 and a heavy chain comprising the amino acid sequence of SEQ ID NO:4, and
(2) purifying the antibody produced by the cells.

7. The formulation of claim 6 wherein the cells are mammalian cells.

8. The formulation of claim 7, wherein the mammalian cells are Chinese hamster ovary cells.

9. An article of manufacture comprising a container enclosing a stable, liquid formulation of low turbidity comprising (a) an anti-IgE antibody in an amount of about 150 mg/ml, (b) arginine-HCl in an amount of 200 mM, (c) histidine in an amount of 20 mM, and (d) polysorbate in an amount of 0.01 to 0.1%, and where the formulation further has a pH of 6.0;
wherein the anti-IgE antibody is produced by a method comprising
(1) culturing cells transformed or transfected with a vector containing nucleic acid encoding an antibody comprising a light chain comprising the amino acid sequence of SEQ ID NO:1 and a heavy chain comprising the amino acid sequence of SEQ ID NO:4, and
(2) purifying the antibody produced by the cells.

10. The article of manufacture of claim 9, wherein the cells are mammalian cells.

11. The article of manufacture of claim 10, wherein the mammalian cells are Chinese hamster ovary cells.

12. The article of manufacture of claim 9, wherein the container is a syringe.

13. The article of manufacture of claim 12, wherein the syringe is further contained within an injection device.

14. The article of manufacture of claim 13, wherein the injection device is an auto-injector.

\* \* \* \* \*